US009066992B2

(12) United States Patent
Stankus et al.

(10) Patent No.: US 9,066,992 B2
(45) Date of Patent: Jun. 30, 2015

(54) POLYMERS FOR IMPLANTABLE DEVICES EXHIBITING SHAPE-MEMORY EFFECTS

(71) Applicant: Abbott Cardiovascular Systems Inc., Santa Clara, CA (US)

(72) Inventors: John J. Stankus, Campbell, CA (US); O. Mikael Trollsas, San Jose, CA (US); Michael H. Ngo, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/903,773

(22) Filed: May 28, 2013

(65) Prior Publication Data

US 2014/0010858 A1 Jan. 9, 2014

Related U.S. Application Data

(63) Continuation of application No. 11/888,940, filed on Aug. 3, 2007, now abandoned.

(51) Int. Cl.
*A61L 27/18* (2006.01)
*A61L 27/34* (2006.01)
*A61L 27/54* (2006.01)
*C08L 75/04* (2006.01)

(52) U.S. Cl.
CPC ............... *A61L 27/18* (2013.01); *A61L 27/34* (2013.01); *A61L 2400/16* (2013.01); *C08G 2230/00* (2013.01); *C08G 2280/00* (2013.01); *C08L 75/04* (2013.01); *A61L 27/54* (2013.01)

(58) Field of Classification Search
CPC C08G 2280/00; C08G 2230/00; C08L 75/04; C08L 75/06; A61L 2400/16; A61L 27/34
USPC ................................................... 528/61, 65
See application file for complete search history.

(56) References Cited

U.S. PATENT DOCUMENTS

| 4,284,506 | A | | 8/1981 | Tetenbaum et al. | |
|---|---|---|---|---|---|
| 5,145,935 | A | | 9/1992 | Hayashi | |
| 5,403,188 | A | | 4/1995 | Oxman et al. | |
| 5,798,421 | A | * | 8/1998 | Corpart et al. | 525/326.9 |
| 6,074,747 | A | * | 6/2000 | Scholz et al. | 428/352 |
| 6,100,310 | A | * | 8/2000 | Ho | 521/159 |
| 6,160,084 | A | | 12/2000 | Langer et al. | |
| 6,211,249 | B1 | * | 4/2001 | Cohn et al. | 514/772.1 |
| 6,221,997 | B1 | | 4/2001 | Woodhouse et al. | |
| 6,281,262 | B1 | | 8/2001 | Shikinami | |
| 6,388,043 | B1 | | 5/2002 | Langer et al. | |
| 6,417,312 | B1 | * | 7/2002 | Kirchmeyer et al. | 528/59 |
| 6,545,384 | B1 | | 4/2003 | Pelrine et al. | |
| 6,639,041 | B2 | * | 10/2003 | Nishikawa et al. | 528/61 |
| 6,777,524 | B1 | | 8/2004 | Shimizu et al. | |
| 6,784,273 | B1 | | 8/2004 | Spaans et al. | |
| 6,841,255 | B2 | | 1/2005 | Deppisch et al. | |
| 6,852,823 | B2 | * | 2/2005 | Sunkara et al. | 528/61 |
| 7,074,850 | B2 | | 7/2006 | Hees et al. | |
| 7,135,128 | B2 | | 11/2006 | Hippold et al. | |
| 7,563,454 | B1 | * | 7/2009 | Pacetti | 424/422 |
| 2001/0009662 | A1 | * | 7/2001 | Cohn et al. | 424/78.17 |
| 2001/0044516 | A1 | | 11/2001 | Kaufhold et al. | |
| 2002/0103325 | A1 | | 8/2002 | Bleys et al. | |
| 2002/0120333 | A1 | * | 8/2002 | Keogh et al. | 623/11.11 |
| 2002/0161114 | A1 | * | 10/2002 | Gunatillake et al. | 525/100 |
| 2003/0078342 | A1 | * | 4/2003 | Harris et al. | 525/91 |
| 2003/0130470 | A1 | | 7/2003 | Bleys et al. | |
| 2004/0014929 | A1 | | 1/2004 | Lendlein et al. | |
| 2004/0015187 | A1 | | 1/2004 | Lendlein et al. | |
| 2004/0110285 | A1 | | 6/2004 | Lendlein et al. | |
| 2004/0116641 | A1 | | 6/2004 | Mather et al. | |
| 2004/0127673 | A1 | | 7/2004 | Sunkara | |
| 2004/0141942 | A1 | * | 7/2004 | Rollat et al. | 424/70.17 |
| 2004/0156819 | A1 | * | 8/2004 | Cohn et al. | 424/78.38 |
| 2004/0210027 | A1 | * | 10/2004 | Hayashi et al. | 528/76 |
| 2005/0021131 | A1 | | 1/2005 | Venkatraman et al. | |
| 2005/0048121 | A1 | | 3/2005 | East et al. | |
| 2005/0107563 | A1 | | 5/2005 | Hu et al. | |
| 2005/0197481 | A1 | * | 9/2005 | Temple et al. | 528/83 |
| 2005/0245719 | A1 | | 11/2005 | Mather et al. | |
| 2006/0036045 | A1 | * | 2/2006 | Wilson et al. | 525/452 |
| 2006/0041089 | A1 | | 2/2006 | Mather et al. | |

(Continued)

FOREIGN PATENT DOCUMENTS

WO    WO 2006/115799    11/2006

OTHER PUBLICATIONS

Huang et al., Biomacromolecules 2002, 3, 397-406.*
Ping et al., Biomacromolecules, 2005, 6, 587-592.*
Asplund et al., Biomacromolecules 2007, 8, 905-911.*
International Search Report for PCT/US2008/071453, mailed Jun. 3, 2009, 15 pgs.
Byung K Kim et al., "Polyurethanes having shape memory effects", Polymer vol. 37, No. 26, pp. 5781-5793 (1996).
Lee et al.,"Synthesis and Gelation of DOPA-Modified Poly(ethylene glycol) I lydrogels", Biomacromolecules 3, pp. 1038-1047 (2002).
Lendlein et al. "Shape-Memory Polymers", Angew. Chem. Int. Ed. 2002, 41, pp. 2034-2057.
Martin et al., "Enhancing the biological activity of immobilized osteopontin using a type-1 collagen affinity coating", J. Biomed. Mater Res 70A, pp. 10-19 (2004).
Polyethylene Glycol 1000 MSDS, Material Safety Data Sheet, Science Lab. com (accessed 2011), 6 pgs.

*Primary Examiner* — Liam J Heincer
(74) *Attorney, Agent, or Firm* — Squire Patton Boggs (US) LLP

(57) ABSTRACT

The present invention is directed to polymeric compositions comprising a biodegradable copolymer that possesses shape-memory properties and implantable devices (e.g., drug-delivery stents) formed of materials (e.g., a coating) containing such compositions. The polymeric compositions can also contain at least one non-fouling moiety, at least additional biocompatible polymer, at least one biobeneficial material, at least one bioactive agent, or a combination thereof. The polymeric compositions are formulated to possess good mechanical, physical and biological properties. Moreover, implantable devices formed of materials comprising such compositions can be delivered to the treatment site in a conveniently compressed size and then can expand to dimensions appropriate for their medical functions.

53 Claims, No Drawings

(56) References Cited

U.S. PATENT DOCUMENTS

| | | |
|---|---|---|
| 2006/0051394 A1 | 3/2006 | Moore et al. |
| 2006/0178497 A1* | 8/2006 | Gevaert et al. ............... 528/44 |
| 2006/0188546 A1 | 8/2006 | Giroux |
| 2006/0216323 A1* | 9/2006 | Knaack et al. ............... 424/422 |
| 2007/0088135 A1 | 4/2007 | Lendlein et al. |
| 2007/0270566 A1 | 11/2007 | Lee et al. |
| 2007/0282435 A1 | 12/2007 | Wang et al. |
| 2008/0208167 A1 | 8/2008 | Stankus et al. |
| 2008/0262613 A1 | 10/2008 | Gogolewski |
| 2008/0268019 A1 | 10/2008 | Badylak et al. |
| 2008/0312315 A1 | 12/2008 | Daniloff et al. |
| 2008/0319132 A1 | 12/2008 | Lendlein et al. |
| 2009/0004243 A1 | 1/2009 | Pacetti et al. |
| 2009/0035350 A1 | 2/2009 | Stankus et al. |
| 2009/0041845 A1 | 2/2009 | Kleiner et al. |
| 2009/0081270 A9* | 3/2009 | Moore et al. ............... 424/423 |
| 2009/0110713 A1 | 4/2009 | Lim et al. |
| 2009/0163664 A1 | 6/2009 | Lendlein et al. |
| 2009/0181063 A1 | 7/2009 | Ngo et al. |
| 2009/0209717 A1* | 8/2009 | Kelch et al. ............... 526/319 |

OTHER PUBLICATIONS

Spagnuolo et al., "Gas 1 is induced by VE-cadherin and vascular endothelial growth factor and inhibits endothelial cell apoptosis", Blood 103, pp. 3005-3012 (2004).

Völkel et al., "Targeting of immunoliposomes to endothelial cells using a single-chain Fv fragment directed against human endoglin (CD105)", Biochemica et Biophysica Acta 1663, pp. 158-166 (2004).

* cited by examiner

POLYMERS FOR IMPLANTABLE DEVICES EXHIBITING SHAPE-MEMORY EFFECTS

CROSS-REFERENCE TO RELATED APPLICATIONS

This application is a continuation of co-pending U.S. application Ser. No. 11/888,940, filed on Aug. 3, 2007, and published as United States Patent Application publication No. 2009-0035350 A1 on Feb. 5, 2009, which is incorporated by reference herein in its entirety, including any drawings, and for all purposes.

BACKGROUND

1. Field of the Invention

The present invention is directed to polymeric materials comprising biodegradable copolymers that exhibit shape-memory effects and implantable devices (e.g., drug-delivery stents) formed of such polymeric materials.

2. Description of the State of the Art

An implantable device that exists in a compressed size and then changes to a shape suitable for a particular medical need upon its deployment would have numerous medical applications (e.g., as a stent). Such a device should exhibit mechanical properties (e.g., strength, rigidity, toughness and flexibility) appropriate for its medical functions. To prevent inflammatory responses to the device and side reactions caused by harmful breakdown products of the device, the device should also biodegrade into biocompatible substances after it accomplishes its medical functions.

As an example, stents are often used in the treatment of atherosclerotic stenosis in blood vessels. To reduce the occlusion of the artery by the collapse of arterial lining and to reduce the chance of thrombosis and restenosis following angioplasty in the vascular system, a stent can be implanted in the lumen to reinforce the blood vessel and maintain the vascular patency. It would be useful if stents are made of a material that allows the stents to exist in a compressed shape, so that they can be inserted through small vessels via catheters, and then allows the stents to self-expand to the desired diameter once they are deployed at the treatment site. To act effectively as a scaffolding, i.e., physically holding open and, if desired, expanding the wall of a passageway, stents must possess good strength, rigidity, toughness and flexibility.

Stents are also used as a vehicle for providing biological therapy. Biological therapy can be achieved by medicating the stents. Medicated stents provide for the local administration of a therapeutic substance at the diseased site, thereby possibly avoiding side effects associated with systemic administration of such substance. One method of medicating stents involves the use of a polymeric carrier coated onto the surface of a stent, where a therapeutic substance is impregnated in the polymeric carrier.

Late stent thrombosis has emerged as a concern for drug-delivery stents. The incidence of late stent thrombosis appears to be higher with drug-delivery stents than with the corresponding bare metal stents. One potential cause of late thrombosis with drug-delivery stents is a chronic inflammatory or hypersensitivity response to the polymeric coating on the stent.

The present invention is directed to biodegradable polymeric materials that exhibit shape-memory effects. Used for making implantable devices (e.g., stents), the polymeric materials enable the devices to adopt the appropriate shape upon deployment in the body, perform their mechanical and therapeutic functions more effectively, and avoid adverse effects such as late stent thrombosis.

SUMMARY OF THE INVENTION

The biodegradable polymeric materials of the invention exhibit shape-memory effects, and thus allow implantable devices made therefrom to exist in desired shapes before and after deployment in the body. The inventive polymeric materials are also configured to completely or substantially completely erode after the devices accomplish their intended functions (e.g., acting as a scaffolding, promoting tissue regeneration, maintaining vascular patency and/or locally delivering drugs), thereby avoiding adverse effects such as inflammatory responses and late stent thrombosis. Other advantages of the polymeric materials include, among others, good mechanical properties (e.g., strength, rigidity, toughness, flexibility and recoverability), biocompatibility, control of drug-release rates, and enhanced adhesion to metal surfaces. The physical and chemical properties of the polymeric materials can be tuned by appropriate selection of the monomer components, the ratios and numbers of the monomers, the molecular weight and length of the various monomer sections, and the arrangement of the various monomers.

Some embodiments of the invention are directed to a composition comprising a biodegradable copolymer comprising at least two segments A and B, wherein:
 the A segment has a $T_g$ or $T_m$ in the range from about 50° C. to about 300° C. and is made from at least one diisocyanate and at least one diol, diamine or dithiol chain extender;
 the B segment has a $T_g$ or $T_m$ in the range from about 30° C. to about 100° C. and is derived from a polymer containing at least one hydroxyl, amino or thiol end group;
 the $T_g$ or $T_m$ of the A segment is at least about 20° C. greater than the $T_g$ or $T_m$ of the B segment; and
 the A and B segments each independently have a polymer number-average molecular weight ($M_n$) from about 0.4 kDa to about 500 kDa;
and wherein:
 the composition displays at least one shape-memory effect, and
 a permanent shape of the composition is obtained when the temperature of the composition is equal to or greater than the $T_g$ or $T_m$ of the B segment.

The copolymer may be thermoplastic or thermoset, and the B segment may be miscible or immiscible with the A segment.

In another embodiment, the biodegradable copolymer further comprises a third segment A', wherein the A' segment:
 is made from at least one diisocyanate and at least one diol, diamine or dithiol chain extender;
 has an $M_n$ from about 0.4 kDa to about 500 kDa;
 may be attached to the B segment or the A segment; and
 may be the same as or different than the A segment.

In an embodiment, the A' segment has a $T_g$ or $T_m$ in the range from about −70° C. to about 100° C.

In yet another embodiment, the A and B segments (and the A' segment, if applicable) each independently comprise a polymer comprising from one to four different types of monomer, wherein each type of monomer has from about 5 to about 5,000 monomer units.

In one embodiment, the B segment is derived from a polyester containing at least one hydroxyl end group. In another embodiment, the B segment further comprises at least one non-fouling moiety. In still another embodiment, the A segment (and the A' segment, if applicable) is made from at least one aliphatic diisocyanate.

In a further embodiment, at least one dihydroxyaryl group is conjugated to the polymer ends of the biodegradable copolymer to enhance adhesion of the copolymer to metal surfaces.

In another embodiment, the composition of the invention further comprises at least one additional biocompatible polymer.

In yet another embodiment, the composition further comprises at least one biobeneficial material.

In some embodiments, the composition further comprises at least one biologically active agent. In an embodiment, the at least one biologically active agent is selected from antiproliferative, antineoplastic, anti-inflammatory, antiplatelet, anticoagulant, antifibrin, antithrombin, antimitotic, antibiotic, antiallergic and antioxidant substances.

According to another embodiment, the at least one biologically active agent is selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, bioactive RGD, CD-34 antibody, abciximab (REOPRO), progenitor cell-capturing antibodies, prohealing drugs, prodrugs thereof, co-drugs thereof, and a combination thereof.

Other embodiments of the invention are directed to a coating comprising any combination of embodiments of the inventive composition.

Yet other embodiments of the invention are directed to an implantable device formed of a material comprising any combination of embodiments of the inventive composition. In an embodiment, the material comprises any combination of embodiments of the inventive coating, which is disposed over the implantable device. In another embodiment, the implantable device is a stent, graft, stent-graft, catheter, lead, electrode, clip, shunt, closure device, or valve.

Still other embodiments of the invention are directed to a method of preparing any combination of embodiments of the inventive composition by performing polycondensation with the corresponding diisocyanate(s) and the corresponding diol, diamine and/or dithiol chain extender(s) for the A segment (and the A' segment, if applicable).

Further embodiments of the invention are directed to a method of fabricating an implantable device. In one embodiment, the method comprises forming the implantable device of a material comprising any combination of embodiments of the inventive composition. In another embodiment, the method comprises depositing any combination of embodiments of the inventive coating over at least a portion of the implantable device. In certain embodiments, the implantable device is a stent, graft, stent-graft, catheter, lead, electrode, clip, shunt, closure device, or valve.

Still further embodiments of the invention are directed to a method of treating or preventing a condition or disorder in a patient, comprising implanting in the patient any combination of embodiments of the inventive implantable device. In certain embodiments, the method further comprises providing a thermal stimulus to the implantable device to induce formation of the permanent shape of the device in cases where the $T_g$ or $T_m$ of the B segment is greater than the body temperature of the particular patient. In an embodiment, the condition or disorder is selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a more specific embodiment, the condition or disorder is selected from atherosclerosis, thrombosis, restenosis, and vulnerable plaque.

Various embodiments of the invention are described in further detail below.

DETAILED DESCRIPTION OF THE INVENTION

Terms and Definitions

The following definitions apply:

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Complete" degradation of a polymer or a polymeric material (e.g., a polymeric coating) means that the polymer or the polymeric material loses at least about 95% of its mass over a period of time.

"Substantially complete" degradation of a polymer or a polymeric material (e.g., a polymeric coating) means that the polymer or the polymeric material loses at least about 75% of its mass over a period of time. In certain embodiments, "substantially complete" degradation of a polymer or a polymeric material can mean that the polymer or the polymeric material loses at least about 80% of its mass, or at least about 85% of its mass, or at least about 90% of its mass, or at least about 95% of its mass over a period of time.

As used herein, a "biocompatible" polymer refers to a polymer that is capable of enhancing the biological compatibility of the composition, material (e.g., coating) or structure (e.g., implantable device) containing it by not causing injury or toxicity to, or an immunological reaction in, living tissue.

A "biobeneficial" material refers to a material that benefits a treatment site (e.g., by enhancing the biocompatibility of the medical device containing such material) by being non-fouling, hemocompatible, non-thrombogenic, and/or anti-inflammatory, etc., without depending on the release of a pharmaceutically or therapeutically active agent.

A "non-fouling moiety" refers to a portion of a composition of this invention that provides an implantable device fabricated from or coated with the composition with the ability to resist (i.e., to prevent, delay, or reduce the amount of) build-up of a denatured layer of protein on its surface, which is caused by the body's reaction to foreign material and can lead to protein fouling. Protein fouling occurs when proteins aggregate on the surface of the material. Protein aggregation can occur due to hydrophobic interactions and when a protein is reversibly or irreversibly denatured when hydrophobic regions of the protein are exposed due to interaction with the material. Protein aggregation can also result from oxidation of thiol groups on proteins to form covalent aggregates.

The adsorption of proteins on the surface of an implanted device constitutes the first step of several biological responses, including the activation of the coagulation cascade. Following protein adsorption, cell adhesion occurs, which could lead to impairment of the device's functioning as well as adverse side effects on the patient. For example, thrombi formation could occur after adsorption and activation of platelets.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses those cases where the physiological conditions (e.g., body temperature) of an animal are not considered "normal".

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug can exert an effect different from that of the other drug, or it can promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.,* 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.,* 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs,* 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

The terms "block copolymer" and "graft copolymer" are defined in accordance with the terminology used by the International Union of Pure and Applied Chemistry (IUPAC). "Block copolymer" refers to a copolymer containing a linear arrangement of blocks. The block is defined as a portion of a polymer molecule in which the monomer units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

As used herein, an "implantable device" can be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, and cerebrospinal fluid shunts. The stents can be intended for any vessel in the body, including neurological, carotid, vein graft, coronary, aortic, renal, iliac, femoral, popliteal vasculature, and urethral passages.

An implantable device can be designed for the localized delivery of a therapeutic agent. A medicated implantable device can be constructed in part, e.g., by coating the device with a coating material containing a therapeutic agent. The body of the device can also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a "portion" of an implantable device can be any portion of the device. For example, a portion can be a portion of the body of the device. As another example, a portion can be a portion of the surface of the device, or the whole surface of the device. As a further example, a portion can refer to an area of material in the body or over the surface of the device, e.g., a layer, film or coating disposed over the device.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon-expandable stent, the stent is mounted about a balloon disposed on the catheter. Mounting the stent typically involves compressing or crimping the stent onto the balloon. The stent is then expanded by inflating the balloon. The balloon can then be deflated and the catheter withdrawn. In the case of a self-expanding stent, the stent can be secured to the catheter via a constraining member such as a retractable sheath or a sock. When the stent is in a desired bodily location, the sheath can be withdrawn, which allows the stent to self-expand.

The "glass transition temperature", $T_g$, is the temperature at which the amorphous domains of a polymer change from a brittle, glassy, vitreous state to a solid deformable, ductile or rubbery state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. The $T_g$ of a given polymer can be dependent on the heating rate and can be influenced by the thermal history of the polymer. Furthermore, the chemical structure of the polymer heavily influences the glass transition by affecting chain mobility.

The "melting temperature", $T_m$, is the temperature at which the crystalline domains of a polymer lose their short- and long-term order, changing from a regular, ordered structure of chain packing to that of a disordered structure, resembling an amorphous polymer. The disappearance of the polymer crystalline phase is accompanied by changes in physical properties of the polymer. The material becomes a viscous solid, with discontinuous changes in the density, refractive index, heat capacity, transparency, and other properties. The $T_m$ of a given polymer occurs over a finite temperature range. The breadth of the transition is dependent on the size and perfection of the polymer crystallites, as well as their homogeneity and purity. By thermal analytical techniques, the $T_m$ of a semi-crystalline polymer is an endothermic transition when the heating rate is positive. The ability of the polymer chains to pack into an ordered, repeating structure is heavily influenced by the chemical structure of the polymer.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" can be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its $T_g$, a polymer tends to be brittle with a high modulus. As the temperature of a polymer is increased from below to above its $T_g$, its modulus decreases.

"Strain" refers to the amount of elongation or compression that occurs in a material at a given stress or load.

"Elongation" can be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

The terms "alkyl" and "aliphatic group" refer to an optionally substituted, straight-chain or branched, saturated or unsaturated hydrocarbon moiety that may contain one or more heteroatoms selected from O, S, and N. If unsaturated, the alkyl or aliphatic group may contain one or more double bonds and/or one or more triple bonds. The alkyl or aliphatic group may be monovalent (i.e., —R) or divalent (i.e., —R—) in terms of its attachment to the rest of the compound. Examples of alkyl and aliphatic groups include, but are not limited to, methyl, ethyl, ethylenyl, ethynyl, n-propyl, isopropyl, propenyl, propynyl, n-butyl, isobutyl, sec-butyl, tertiary-butyl, butenyl, butyryl, n-pentyl, isopentyl, pentenyl, and pentynyl.

The terms "heteroalkyl" and "heteroaliphatic group" refer to an alkyl or aliphatic group that contains at least one heteroatom selected from O, S and N, in the main portion and/or the branch(es) of the hydrocarbon moiety. Examples of heteroalkyl and heteroaliphatic groups include, but are not limited to, alcohols, ethers, oxo compounds, ketones, aldehydes, esters, carbonates, thioesters, thiols, sulfides, sulfoxides, sulfones, sulfonamides, amino compounds, amines, nitriles, N-oxides, imines, oximes, amides, carbamates, ureas, and thioureas.

The terms "cycloalkyl" and "cycloaliphatic group" refer to an optionally substituted, saturated or unsaturated, mono- or polycyclic hydrocarbon moiety that may contain one or more heteroatoms selected from O, S, and N. If unsaturated, the cycloalkyl or cycloaliphatic group may contain one or more double bonds and/or one or more triple bonds in and/or off of one or more rings of the cyclic moiety. The cycloalkyl or cycloaliphatic group may be monovalent (i.e., -Cyc) or divalent (i.e., -Cyc-) in terms of its attachment to the rest of the compound. Examples of cycloalkyl and cycloaliphatic groups include, but are not limited to, cyclopropyl, cyclobutyl, cyclopentyl, cyclopentenyl, cyclohexyl, cyclohexenyl, decahydronaphthyl, and octahydroindyl.

The terms "heterocycloalkyl" and "heterocycloaliphatic group" refer to a cycloalkyl or cycloaliphatic group in which at least one ring in the cyclic moiety contains one or more heteroatoms selected from O, S, and N. Examples of heterocycloalkyl and heterocycloaliphatic groups include, but are not limited to, aziridinyl, oxiranyl, oxolanyl, thiolanyl, pyrrolidinyl, 3-pyrrolinyl, dioxalanyl, 1,3-dithiolanyl, oxazolidinyl, imidazolidinyl, oxanyl, piperidinyl, piperazinyl, 1,3-dioxanyl, 1,4-dioxanyl, morpholinyl, octahydroindolyl, octahydroisoindolyl, octahydrobenzofuryl, octahydrobenzothiophene, octahydrochromenyl, and decahydroquinolinyl.

The terms "aryl" and "aromatic group" refer to an optionally substituted mono- or polycyclic aromatic moiety in which at least one ring in the moiety is aromatic. The ring(s) in the moiety may be carbocyclic or may contain one or more heteroatoms selected from O, S, and N. The ring(s) in the moiety may be aromatic or non-aromatic (saturated or unsaturated), but at least one ring in the moiety is aromatic. An aryl or aromatic group may be monovalent (i.e., —Ar) or divalent (i.e., —Ar—) in terms of its attachment to the rest of the compound. Examples of aryl and aromatic groups include, but are not limited to, phenyl, indolinyl, isoindolinyl, 2,3-dihydrobenzofuryl, 2,3-dihydrobenzothiophene, chromanyl, 1,2,3,4-tetrahydroquinolinyl, 1,2,3,4-tetrahydroisoquinolinyl, naphthyl, indenyl, and indanyl.

The terms "heteroaryl" and "heteroaromatic group" refer to an aryl or aromatic group in which at least one ring (aromatic or non-aromatic) in the aromatic moiety contains one or more heteroatoms selected from O, S, and N. Examples of heteroaryl and heteroaromatic groups include, but are not limited to, pyrrolyl, pyrazolyl, imidazolyl, furyl, isoxazolyl, oxazolyl, thiophenyl, thiazolyl, isothiazolyl, triazolyl, oxadiazolyl, thiadiazolyl, tetrazolyl, pyridyl, pyridazinyl, pyrimidinyl, pyrazinyl, 1,3,5-triazinyl, indolyl, isoindolyl, benzofuranyl, benzothiophenyl, indazolyl, benzimidazolyl, benzothiazolyl, [1,7]naphthyridinyl, chromenyl, quinolinyl, isoquinolinyl, cinnolinyl, quinazolinyl, quinoxalinyl, phthalazinyl, purinyl, pyridazinyl, quinolinyl, imidazo[4,5-c]pyridinyl, pyrido[2,3-d]pyrimidinyl, pyrimido[3,2-c]pyrimidinyl, and pyrrolo[2,3-d]pyrimidinyl.

The alkyl, aliphatic, heteroalkyl, heteroaliphatic, cycloalkyl, cycloaliphatic, heterocycloalkyl, heterocycloaliphatic, aryl, aromatic, heteroaryl and heteroaromatic groups may be substituted or unsubstituted. If substituted, they may contain from 1 to 5 substituents. The substituents include, but are not limited to: optionally substituted carbon-containing groups, e.g., alkyl, cycloalkyl and aryl (e.g., benzyl); halogen atoms (i.e., F, Cl, Br and I) and optionally substituted halogen-containing groups, e.g., haloalkyl (e.g., trifluoromethyl); optionally substituted oxygen-containing groups, e.g., oxo, alcohols (e.g., hydroxyl, hydroxyalkyl, aryl (hydroxyl)alkyl), and ethers (e.g., alkoxy, aryloxy, alkoxyalkyl, aryloxyalkyl); optionally substituted carbonyl-containing groups, e.g., aldehydes (e.g., carboxaldehyde), ketones (e.g., alkylcarbonyl, alkylcarbonylalkyl, arylcarbonyl, arylalkylcarbonyl, arycarbonylalkyl), carboxy acids (e.g., carboxy, carboxyalkyl), esters (e.g., alkoxycarbonyl, alkoxycarbonylalkyl, alkylcarbonyloxy, alkylcarbonyloxyalkyl), carbonates, thioesters, amides (e.g., aminocarbonyl, mono- or dialkylaminocarbonyl, aminocarbonylalkyl, mono- or dialkylaminocarbonylalkyl, arylaminocarbonyl, alkylarylaminocarbonyl), carbamates (e.g., alkoxycarbonylamino, aryloxycarbonylamino, aminocarbonyloxy, mono- or dialkylaminocarbonyloxy, arylaminocarbonyloxy, alkylarylaminocarbonyloxy), and ureas (e.g., mono- or dialkylaminocarbonylamino, arylaminocarbonylamino, alkylarylaminocarbonylamino); optionally substituted groups containing carbonyl derivatives, e.g., imines, oximes, and thioureas; optionally substituted nitrogen-containing groups, e.g., amines (e.g., amino, mono- or dialkylamino, mono- or diarylamino, alkylarylamino, aminoalkyl, mono- or dialkylaminoalkyl), azides, nitriles (e.g., cyano, cyanoalkyl) and nitro; optionally substituted sulfur-containing groups, e.g., thiols, sulfides, thioethers, sulfoxides, sulfones and sulfonamides (e.g. sulfhydryl, alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and optionally substituted aromatic or non-aromatic heterocyclic groups containing one or more heteroatoms selected from O, S and N (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl, carbolinyl).

Shape-Memory Characteristics

A polymeric material displaying shape-memory effects can have two or more phases or segments. If the polymer has two segments, the "harder" segment with the higher $T_g$ or $T_m$ acts as the crosslink and is responsible for the permanent shape of the material. Crosslinks to provide the permanent shape can be physical (e.g., microphase separation, hydrogen bonding, or crystalline melting temperature) or covalent (crosslinking) Thermoplastic polymers tend to have physical crosslinks, while thermoset polymers tend to have covalent crosslinks. The harder segment provides strength and rigidity to the material. At a temperature at or above the $T_g$ or $T_m$ of the harder segment, the material loses its permanent shape and becomes amorphous or fluid-like.

The other, "softer" segment is responsible for the temporary shape of the material at a temperature below the $T_g$ or $T_m$ of this segment. At a temperature at or above the $T_g$ or $T_m$ of the softer segment, the material transitions to its permanent shape. In other words, the transition, or switching, temperature of the material is the melting temperature, $T_m$ (if the segment is crystalline), or the glass transition temperature, $T_g$ (if the segment is partially crystalline, glassy, non-crystalline, or amorphous), of the softer segment. The softer segment tends to be more flexible and elastic than the harder segment so that the former can facilitate the transition from the temporary shape to the permanent shape.

If the shape-memory polymer contains three segments, an article formed of such a polymer can have one permanent shape and two temporary shapes. The third, "softest" segment would be responsible for a second temporary shape, and the article would switch to its first temporary shape at a temperature at or above the $T_g$ or $T_m$ of the softest segment.

In summary, an article formed of a two-segment, shape-memory polymer can have one permanent shape and one temporary shape. If a temporary shape was never created, the permanent shape of the article exists at a temperature below the $T_g$ or $T_m$ of the harder segment. If a temporary shape was created, the temporary shape exists at a temperature below the $T_g$ or $T_m$ of the softer segment, and the permanent shape is recovered in the temperature range from, and including, the $T_g$ or $T_m$ of the softer segment to below the $T_g$ or $T_m$ of the harder segment.

If the shape-memory polymer contains a third, "softest" segment, then the article can have a second temporary shape. If a second temporary shape was never created, the (first) temporary shape exists at a temperature below the $T_g$ or $T_m$ of the softer segment. If a second temporary shape was created, the second temporary shape exists at a temperature below the $T_g$ or $T_m$ of the softest segment, and the first temporary shape exists in the temperature range from, and including, the $T_g$ or $T_m$ of the softest segment to below the $T_g$ or $T_m$ of the softer segment. Again, the permanent shape is recovered in the temperature range from, and including, the $T_g$ or $T_m$ of the softer segment to below the $T_g$ or $T_m$ of the harder segment.

Embodiments of the Invention

Composition And Polymer

Some embodiments of the present invention are directed to a polymeric composition that displays shape-memory effects and is designed to possess properties suitable for implantable devices. The degradation rate of a polymer can be enhanced by the appropriate selection of monomers and ratio thereof for the "harder" and "softer" segments of the polymer. The relatively high $T_g$ or $T_m$ of the "harder" segment, above body temperature (e.g., above about 50° C.), increases the strength and rigidity of the polymer. Further, the fracture toughness, flexibility and drug permeability of the polymer can be increased by incorporation, with the harder segment polymer, of a "softer" segment polymer having a $T_g$ or $T_m$ less than the $T_g$ or $T_m$ of the harder segment polymer.

The softer segment can be designed to have a $T_g$ or $T_m$ of around body temperature or greater, depending upon the particular needs. If the softer segment has a $T_g$ or $T_m$ of around body temperature, then the permanent shape of the polymeric composition, and hence that of the implantable device (e.g., a stent) formed thereof, will be obtained when the device is deployed at the desired bodily location. The softer segment can also be designed to have a $T_g$ or $T_m$ above body temperature for various reasons (e.g., so that the permanent shape is not recovered during sterilization of the device at elevated temperature). In such a case, the permanent shape of the composition can be obtained by providing a thermal stimulus to the composition (e.g., via a catheter). The harder segment can be designed to have a $T_g$ or $T_m$ sufficiently greater (e.g., at least about 20° C. greater) than the $T_g$ or $T_m$ of the softer segment so that the composition, and thus the device, does not lose its desired permanent shape after being deployed in the body.

Accordingly, some embodiments of the present invention, optionally in combination with one or more other embodiments described herein, are directed to a composition comprising a biodegradable copolymer comprising at least two segments A and B, wherein:

the A segment has a $T_g$ or $T_m$ in the range from about 50° C. to about 300° C. and is made from at least one diisocyanate and at least one diol, diamine or dithiol chain extender;

the B segment has a $T_g$ or $T_m$ in the range from about 30° C. to about 100° C. and is derived from a polymer containing at least one hydroxyl, amino or thiol end group;

the $T_g$ or $T_m$ of the A segment is at least about 20° C. greater than the $T_g$ or $T_m$ of the B segment; and the A and B segments each independently have a polymer number-average molecular weight ($M_n$) from about 0.4 kDa to about 500 kDa;

and wherein:

the composition displays at least one shape-memory effect, and a permanent shape of the composition is obtained when the temperature of the composition is equal to or greater than the $T_g$ or $T_m$ of the B segment.

In some cases, the harder A segment might not have a $T_m$ and its $T_g$ may be broad. For example, the A segment may be semi-crystalline or non-crystalline and may not have a $T_m$. A more amorphous A segment may also have a broad $T_g$ that overlaps with the $T_g$ or $T_m$ of the B segment. The scope of the present invention also encompasses those cases where the harder A segment has no $T_m$ and exhibits a broad $T_g$.

In one embodiment, the A segment has a $T_g$ or $T_m$ in the range from about 50° C. to about 300° C. when the A segment is hydrated, and the B segment has a $T_g$ or $T_m$ in the range from about 30° C. to about 100° C. when the B segment is hydrated. In another embodiment, the A segment has a $T_g$ or $T_m$ in the range from about 50° C. to about 300° C. when the A segment is not hydrated, and the B segment has a $T_g$ or $T_m$ in the range from about 30° C. to about 100° C. when the B segment is not hydrated.

The B segment may or may not be miscible with the A segment. In one embodiment, optionally in combination with one or more other embodiments described herein, the B segment is partially or completely miscible with the A segment. In another embodiment, optionally in combination with one or more other embodiments described herein, the B segment is partially or completely immiscible with the A segment. Moreover, the A and/or B segments of the biodegradable copolymer can comprise other polymer(s) that may be partially or completely miscible or immiscible with the B and/or A segments, respectively.

The copolymer exhibiting shape-memory effects can be thermoplastic or thermoset depending on, e.g., the functionality of the monomer components. In one embodiment, the copolymer is thermoplastic. A thermoplastic copolymer can derive desirable mechanical properties from, e.g., microphase separation of the harder and softer segments. In another embodiment, the copolymer of the invention is thermoset. The permanent shape of a material formed of a thermoset copolymer typically is supported by covalent crosslinking between the segments.

The biodegradable copolymer of the invention can comprise elastomeric polymer(s) and/or non-elastomeric polymer(s). In one embodiment, the copolymer comprises at least one elastomeric polymer and no non-elastomeric polymer. In another embodiment, the copolymer comprises at least one non-elastomeric polymer and no elastomeric polymer. In yet another embodiment, the copolymer comprises at least one elastomeric polymer and at least one non-elastomeric polymer.

The segmented nature of the inventive copolymer containing urethane, urea and/or "thiourethane" (i.e., RHNC(O)SR') linkages makes the copolymer suitable for shape-memory programming. For example, the $T_m$ of the harder A segment, if crystalline, can serve as the permanent memory temperature below which the permanent shape memory is set, and the $T_g$ or $T_m$ of the softer B segment can serve as the transition temperature at or above which the permanent shape is recovered. The physical and mechanical properties (e.g., modulus and transition temperature) of the copolymer can be tuned by adjusting various factors, e.g., the length of each segment and the ratio of the monomers of the segments. As an example, a longer harder A segment and a greater ratio of diisocyanate(s) and chain extender(s) of the A segment to the polymer of the softer B segment can lead to a higher modulus and a higher transition temperature.

The softer B segment provides elasticity, allowing the polymeric composition to transition from a temporary shape to the permanent shape when the temperature of the composition is at or above the $T_g$ or $T_m$ of the B segment. On the other hand, the harder A segment provides strength and rigidity for, and thus gives form to, the permanent shape of the composition. Because the A segment is created by at least one polycondensation reaction involving at least one diisocyanate and at least one diol, diamine or dithiol chain extender, the A segment is rich in hydrogen bonds involving the resulting carbamate (or urethane), urea and/or thiourethane linkages. These hydrogen bonds act as virtual crosslinks to give strength and structure to the permanent shape of the composition.

To provide strength and rigidity, and to ensure that the composition, and hence the implantable device formed thereof, does not lose its desired permanent shape under intended or potential conditions of application, the A segment is formulated so that its $T_g$ or $T_m$ is above body temperature. In one embodiment, optionally in combination with one or more other embodiments described herein, the $T_g$ or $T_m$ of the A segment is in the range from about 50° C. to about 300° C. The $T_g$ or $T_m$ of the A segment can be tuned to a desired value by appropriate selection of component monomers and adjustment of their numbers, ratio and arrangement. In certain embodiments, optionally in combination with one or more other embodiments described herein, the $T_g$ or $T_m$ of the A segment ranges from about 50° C. to about 300° C., or from about 60° C. to about 280° C., or from about 70° C. to about 260° C., or from about 80° C. to about 240° C., or from about 90° C. to about 220° C., or from about 100° C. to about 200° C.

The permanent shape of the polymeric composition, and hence that of the implantable device formed thereof, is recovered when the temperature of the composition is at or above the $T_g$ or $T_m$ of the B segment. The $T_g$ or $T_m$ of the B segment should be in a range suitable for the expected conditions of the storage, sterilization and application of the device. In one embodiment, optionally in combination with one or more other embodiments described herein, the $T_g$ or $T_m$ of the B segment is in the range from about 30° C. to about 100° C. The lower end of the range, about 30° C., allows for the recovery of the permanent shape, without an additional thermal stimulus, in a patient whose body temperature is significantly below "normal" body temperature. Further, this lower end avoids the obtainment of the permanent shape when the device is at room temperature. The higher end of the range, about 100° C., should allow for the safe provision of a thermal stimulus for recovering the permanent shape. Exposure of a biological structure (e.g., tissues) to a heat source at about 100° C. should present little risk of damage to that biological structure so long as the thermal stimulus is provided within a short time period (i.e., several seconds).

Provision of a thermal stimulus can also be made safe by appropriate thermal shielding of the implantable device or another article that delivers the device and provides the thermal stimulus. For example, a stent can be delivered through a catheter that contains an outer insulating or cooling component to shield the blood and tissues from the catheter compartment providing the thermal stimulus.

The $T_g$ or $T_m$ of the B segment can be tuned to a desired value by appropriate selection of component monomers and adjustment of their numbers, ratio and arrangement. In certain embodiments, optionally in combination with one or more other embodiments described herein, the $T_g$ or $T_m$ of the B segment ranges from about 30° C. to about 100° C., or from about 40° C. to about 90° C., or from about 50° C. to about 80° C. In a particular embodiment, the B segment has a $T_g$ or $T_m$ in the range from about 35° C. to about 70° C. In another specific embodiment, the B segment has a $T_g$ or $T_m$ around body temperature, so that the permanent shape of the polymeric composition is recovered when the implantable device formed thereof is deployed in the body. Thus, in an embodiment, the $T_g$ or $T_m$ of the B segment is in the range from about 35° C. to about 40° C.

In another embodiment, the B segment has a $T_g$ or $T_m$ significantly greater than body temperature to provide for greater radial strength of the implantable device after its expansion to its permanent shape. In certain embodiments, the B segment has a $T_g$ or $T_m$ that is 5° C., or 10° C., or 15° C., or 20° C., or 25° C., or 30° C., or 35° C. greater than body temperature.

Various terminal sterilization processes are available for sterilizing implantable devices (e.g., drug-delivery stents). Many of these processes, such as electron beam and gamma irradiation, can cause degradation of a drug incorporated with an implantable device. Ethylene oxide gas (EOG) tends to cause less drug degradation. EOG sterilization typically transpires at around 40-45° C. Even if an implantable device formed of a shape-memory polymeric composition is sterilized using EOG at about 40-45° C., the transition temperature of the composition can still be around body temperature. For example, the device (e.g., a stent) can be held in a compressed shape by surrounding the device with, e.g., a sheath or a sock, to avoid recovering the permanent shape of the device during sterilization at elevated temperature.

High rigidity and strength may be important for an implantable device formed of a polymeric material, e.g., for a stent so that the stent can support the walls of a vessel. However, the polymeric material should also possess sufficient toughness and flexibility for the range of applications intended for the device. If the device is also intended to deliver a therapeutic agent, the polymeric material should also have sufficient drug permeability to be able to control drug-release rates at reasonable drug-to-polymer ratios. To increase fracture toughness and flexibility and to improve drug-release control, the softer B segment of the biodegradable copolymer can be formulated to have a $T_g$ or $T_m$ less than the $T_g$ or $T_m$ of the harder A segment.

The softer B segment can have greater flexibility, a lower modulus, and higher fracture toughness than the harder A segment at physiological conditions. Examples of biodegradable polymers having a relatively high fracture toughness at body temperature include, but are not limited to, polycaprolactone (PCL), poly(trimethylene carbonate) (PTMC), polydioxanone, poly(propiolactone), poly(valerolactone) and polyacetal. Accordingly, some embodiments of the B segment can include caprolactone (CL), trimethylene carbonate (TMC), dioxanone, propiolactone, valerolactone or acetal monomer units, or a combination thereof.

The A segment can be designed to have a $T_g$ or $T_m$ sufficiently greater than the $T_g$ or $T_m$ of the B segment so that the polymeric composition, and hence the implantable device formed thereof, does not lose its permanent shape under the expected conditions of deployment and application in the body. In certain embodiments, optionally in combination with one or more other embodiments described herein, the $T_g$ or $T_m$ of the A segment is greater than the $T_g$ or $T_m$ of the B segment by at least about 20° C., or by at least about 30° C., or by at least about 40° C., or by at least about 50° C., or by at least about 60° C., or by at least about 70° C.

The mechanical properties (e.g., rigidity, strength, toughness, flexibility and shape-memory recoverability), degradation rate and drug permeability of the inventive copolymer, as well as the $T_g$ or $T_m$ of the segments, can be tuned by appropriate selection of the monomer units of the harder and softer segments, the ratio of the monomers within the segments, the length or molecular weight of the segments, the weight ratio of the segments, and any other substance(s) chemically or non-chemically incorporated with the copolymer.

Any biocompatible polymer that contains at least one hydroxyl, amino or thiol end group and is capable of reacting with a diisocyanate can be used to form the B segment. To enhance the biodegradation of the inventive copolymer, the B segment can be formulated to contain hydrolytically labile bonds. For example, the B segment polymer can be derived from monomer(s) that have a relatively high degradation rate due to their hydrophilic and/or hydrolytically active nature, e.g., poly(glycolide) (PGA) or a glycolide-containing copolymer {e.g., poly(D,L-lactide-co-glycolide (PLGA) and poly(glycolide-co-trimethylene carbonate) (P(GA-co-TMC))}. Thus, if the B segment comprises a glycolide-containing copolymer, the degradation rate of the B segment, and hence that of the polymeric composition, can be increased by augmenting the fraction of GA in the B segment. In exemplary embodiments, a glycolide-containing copolymer of the B segment (e.g., poly(GA-co-CL) or poly(GA-co-TMC)) can have greater than 1 wt %, 5 wt %, 10 wt %, 20 wt %, 30 wt %, 40 wt %, 50 wt %, 60 wt %, 70 wt % or 80 wt % GA units.

Moreover, the B segment can contain monomer units that have acidic or hydrophilic degradation products. Since the rate of the hydrolysis reaction tends to increase as the pH decreases, acidic degradation products can increase the degradation rate of the polymeric material, and hence that of the device formed thereof. For example, glycolide units have acidic degradation products that can increase the degradation rate of a glycolide-containing polymeric material.

In some embodiments, the softer B segment can include toughness-enhancing units and fast degrading units. In more specific embodiments, the B segment can include glycolide (GA), caprolactone (CL), trimethylene carbonate (TMC), valerolactone, propiolactone or acetal units, or a combination thereof. The B segment can have alternating or random GA, CL, TMC, valerolactone, propiolactone and acetal units. For example, the B segment can be poly(GA-co-CL), poly(GA-co-TMC), poly(CL-co-TMC), or poly(GA-co-TMC-co-CL).

The flexibility, toughness and degradation rate of the softer B segment can also be adjusted by the ratio of fast degrading and toughness-enhancing units. For example, as the ratio of CL increases in poly(GA-co-CL), the segment copolymer becomes more flexible and tougher.

In certain embodiments, optionally in combination with one or more other embodiments described herein, the B segment is derived from a polyester containing at least one hydroxyl end group. In one embodiment, the polyester containing at least one hydroxyl end group is selected from polycaprolactone (PCL) diol, poly(β-hydroxy-alkanoate-diol), poly([R]-3-hydroxybutyrate-diol), poly(L-lactide) (PLLA) diol, poly(D,L-lactide) diol, polyglycolic acid, polyglycolide (PGA) diol, poly(trimethylene carbonate) (PTMC) diol, polydioxanone diol, polyvalerolactone diol, polypropiolactone diol, and hydroxyl-terminated random or block copolymers thereof. In a particular embodiment, the hydroxyl-terminated random or block copolymer is selected from poly(D,L-lactide-co-glycolide), poly(L-lactide-co-glycolide), poly(L-lactide-co-caprolactone-co-L-lactide), poly(L-lactide-co-D,L-lactide-co-glycolide-co-L-lactide), poly(glycolide-co-trimethylene carbonate), poly(glycolide-co-caprolactone), poly(caprolactone-co-trimethylene carbonate), poly(glycolide-co-trimethylene carbonate-co-caprolactone), and any variations in the arrangement of the monomers thereof.

The B segment can also be derived from other types of polymers. Non-limiting examples of other types of polymers that can be suitable for forming the B segment include carboxyl-terminated poly(anhydrides), polythioesters and polyacetals.

Moreover, the B segment can comprise at least one non-fouling moiety. In one embodiment, the B segment comprises at least one non-fouling moiety as a main component of the segment. In another embodiment, the B segment comprises at least one non-fouling moiety as an additional component of the segment.

Examples of non-fouling moieties include, without limitation, poly(ethylene glycol) (PEG), poly(propylene glycol), polyethylene oxide, PLURONICTM surfactants (polypropylene oxide-co-PEG), PEO-PPO surfactants (PLURONICTM polyols, poly(ethylene oxide-co-propylene oxide)), poly(tetramethylene glycol), amino-terminated PEG, hydroxy functionalized poly(vinyl pyrrolidone), dextran, dextrin, sulfonated dextran, dermatan sulfate, silk-elastin block copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP) (e.g., R7), phosphoryl choline, heparin, chondroitan sulfate, glycosaminoglycans, chitosan, and derivatives thereof.

Silk and elastin both are natural proteins. Silk possesses strength and elastin high flexibility. Their combination in a block copolymer makes the non-fouling moiety very strong and, at the same time, very flexible. Silk-elastin blockcopolymer can be obtained from Protein Polymer Technologies, Inc. of San Diego, Calif.

In a specific embodiment, the at least one non-fouling moiety is selected from polyethylene glycol (PEG), polypropylene glycol, PluronicTM surfactants (polypropylene oxide-co-PEG), poly(2-hydroxyethyl methacrylate) (PHEMA), poly(vinyl alcohol) (PVA), polyalkene oxides, poly(n-propylmethacrylamide), poly(N-vinyl-2-pyrrolidone) (PVP), sulfonated polystyrene, dextran, sulfonated dextran, dextrin, hyaluronic acid, sodium hyaluronate, and derivatives thereof.

In some embodiments, optionally in combination with one or more other embodiments described herein, the B segment specifically cannot comprise one or more of any of the polymers or substances described herein.

The maximum molecular weight of the non-fouling moiety or, if the non-fouling moiety itself is biodegradable, the maximum molecular weight of the largest fragment formed should be low enough so that it is small enough to pass through the kidneys. Thus, in certain embodiments, the molecular weight of the non-fouling moiety or its largest fragment is 40 kDa or less, or 30 kDa or less, or 20 kDa or less.

Both the at least one diisocyanate and the at least one chain extender used to make the A segment independently can contain an optionally substituted aliphatic, heteroaliphatic, cycloaliphatic, heterocycloaliphatic, aromatic or heteroaromatic group, or a combination thereof. To increase the hydrolytic lability and bioresorbability of a polymer containing urethane, urea and/or thiourethane linkages, appropriate diisocyanates (e.g., aliphatic diisocyanates) and chain extenders (e.g., enzyme-sensitive chain extenders) can be used. Employing aliphatic diisocyanates may have the additional advantage of avoiding potential toxicity associated with aromatic diamine degradation products of aromatic diisocyanates. Therefore, in an embodiment, optionally in combination with one or more other embodiments described herein, the A segment is made from at least one aliphatic diisocyanate.

Non-limiting examples of aliphatic diisocyanates that can be used to make biodegradable polyurethanes, polyureas or polythiourethanes that degrade into biocompatible products include:

1,2-diisocyanatoethane, which hydrolytically degrades into non-carcinogenic ethylene diamine;
1,4-diisocyanatobutane (BDI), which degrades into 1,4-butanediamine (putrescine), a biocompatible mediator of cell growth and differentiation;
1,4-diisocyanatocubane;
1,5-diisocyanatopentane, which degrades into cadaverene, a biological substance found in decomposing tissues;
1,6-diisocyanatohexane, which degrades into 1,6-hexanediamine; and
lysine diisocyanate, which degrades into the amino acid lysine.

Accordingly, in an embodiment, optionally in combination with one or more other embodiments described herein, the A segment is made from at least one aliphatic diisocyanate selected from 1,2-diisocyanatoethane, 1,3-diisocyanatopropane, 1,4-diisocyanatobutane, 1,5-diisocyanatopentane, 1,6-diisocyanatohexane, 1,4-diisocyanatocubane, and lysine diisocyanate.

Other types of diisocyanates can also be utilized to make the A segment. For example, diisocyanates incorporating labile ester bonds can be used to render the A segment more biodegradable.

Various types of diol, diamine and/or dithiol chain extenders can be employed to make the A segment more biodegradable and provide it with strength and shape-memory recoverability. In one embodiment, optionally in combination with one or more other embodiments described herein, the A segment is made from at least one chain extender selected from ethylene glycol, 1,3-propanediol, 1,2-propanediol, 1,4-butanediol (BDO), 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,2-cyclohexanedimethanol, 1,4-cyclohexanedimethanol, the corresponding diamine and dithiol analogs thereof, lysine ethyl ester, arginine ethyl ester, and p-alanine-based diamine.

In another embodiment, optionally in combination with one or more other embodiments described herein, the at least one chain extender includes random or block copolymers made from at least one diisocyanate and at least one diol, diamine or dithiol chain extender. For example, BDO-BDI-BDO and BDI-BDO-BDI-BDO-BDI can be employed to prevent transesterification reactions from causing too much polydispersity within the harder A segment.

Other types of chain extenders can also be utilized to make the A segment. For example, chain extenders incorporating labile ester bonds can be used to render the A segment more biodegradable.

In some embodiments, optionally in combination with one or more other embodiments described herein, the A segment specifically cannot be made from one or more of any of the diisocyanates or from one or more of any of the chain extenders described herein.

For forming certain types of material (e.g., films), the entire polymer may need to have sufficient molecular weight. Accordingly, in some embodiments, optionally in combination with one or more other embodiments described herein, the copolymer of the invention has a polymer number-average molecular weight ($M_n$) of at least about 20 kDa. In other embodiments, the copolymer has an $M_n$ of at least about 40 kDa.

In an embodiment, optionally in combination with one or more other embodiments described herein, the copolymer of the invention ranges in $M_n$ from about 20 kDa to about 1,000 kDa. In another embodiment, the copolymer ranges in $M_n$ from about 20 kDa to about 500 kDa. A polymer with an $M_n$ from about 20 kDa to about 500 kDa may be more amenable to being processed into a coating. In yet another embodiment, the copolymer ranges in $M_n$ from about 40 kDa to about 500 kDa.

For the segments to form discrete phases which are indicative of an immiscible system, they need to be of a certain minimal size. When a two-phase system forms, each phase is saturated with the other phase, although these saturated concentrations may be very small. Accordingly, in some embodiments, the A and B segments each independently have an $M_n$ of at least about 0.4 kDa. In certain embodiments, optionally in combination with one or more other embodiments described herein, the A and B segments each independently range in $M_n$ from about 0.4 kDa to about 500 kDa, or from about 1 kDa to about 500 kDa, or from about 10 kDa to about 400 kDa, or from about 20 kDa to about 300 kDa, or from about 30 kDa to about 200 kDa, or from about 40 kDa to about 100 kDa.

In addition, varying the ratio of softer to harder segments allows one to tune/modify the properties of the polymeric material, e.g., the strength, rigidity, toughness, flexibility, recoverability, drug permeability and biodegradation rate of the material. Accordingly, in certain embodiments, optionally in combination with one or more other embodiments described herein, the ratio of the molecular weight of the A segment to the B segment is between about 20:1 and about 1:20, or between about 10:1 and about 1:10, or between about 5:1 and about 1:5.

In other embodiments, optionally in combination with one or more other embodiments described herein, the weight fraction of the A segment with respect to the total copolymer of the invention is from about 1% to about 99%, or from about 10% to about 90%, or from about 20% to about 80%, or from about 30% to about 70%, of from about 40% to about 60%. In yet other embodiments, the inventive copolymer can contain about 1-50 wt %, or about 5-40 wt %, or about 10-30 wt % of the B segment, and about 50-99% wt %, or about 60-95 wt %, or about 70-90 wt % of the A segment.

In further embodiments, optionally in combination with one or more other embodiments described herein, the A and B segments each independently comprise a polymer comprising from one to four different types of monomer, wherein each type of monomer has from about 5 to about 5,000 monomer units. In narrower embodiments, each type of monomer in the polymer of the A or B segment independently has from about 10 to about 4,500 monomer units, or from about 20 to about 4,000 monomer units, or from about 30 to about 3,500 monomer units, or from about 40 to about 3,000 monomer units, or from about 50 to about 2,500 monomer units.

In another embodiment, optionally in combination with one or more other embodiments described herein, the A segment is made from one to four different polycondensation reactions involving a diisocyanate and a diol, diamine or dithiol chain extender, wherein each polycondensation reaction:
occurs from about 5 to about 5,000 times, and
involves a diisocyanate and a diol, diamine or dithiol chain extender that may be the same as or different than any other diisocyanate(s) and any other diol, diamine or dithiol chain extender(s) involved in any other polycondensation reaction(s).

Adhesion of a polymeric material (e.g., a coating) to a metal surface (e.g., a stent) can be promoted by appropriate (e.g., chemical) modification of the polymer. Such modification could lead to a single polymer, which could be used as a drug reservoir, with no primer. In the case of a polymer that does not have any inherent adhesion to metal surfaces, a primer of that pure polymer may have to be used to achieve optimum adhesion to metal stents.

To improve adhesion of the inventive copolymer to metal surfaces, at least one dihydroxyaryl group could be conjugated to the ends of the copolymer. The dihydroxyaryl group(s) can contain a dihydroxyphenyl moiety. Ortho-dihydroxyphenyl groups in 3,4-dihydroxyphenyl alanine have been shown to be responsible for the bonding of mussel adhesive proteins to a variety of metallic substrates. B. P. Lee et al., *Biomacromolecules*, 3: 1038-1047 (2002). Other 3,4-dihydroxyphenyl-containing compounds that can be conjugated to the ends of the copolymer to increase its adhesion to metal surfaces include, e.g., dopamine and 3,4-dihydroxyhydrocinnamic acid.

Accordingly, in some embodiments, optionally in combination with one or more other embodiments described herein, at least one dihydroxyaryl group is conjugated to the ends of the copolymer of the invention. In an embodiment, the at least one dihydroxyaryl group contains an ortho-dihydroxyphenyl moiety. In one embodiment, the at least one dihydroxyaryl group contains a 1,2-dihydroxyphenyl moiety. In another embodiment, the at least one dihydroxyaryl group contains a 3,4-dihydroxyphenyl moiety. 3,4-Dihydroxyphenyl-containing compounds that could be conjugated to the ends of the copolymer include, e.g., dopamine and 3,4-dihydroxyhydrocinnamic acid.

As explained earlier, if a shape-memory polymer contains three segments, it can have one permanent shape and two temporary shapes. The permanent shape would be recovered upon deployment of the implantable device formed of that polymer, with the provision of a thermal stimulus, if necessary. A first temporary shape may be desired, e.g., for handling of the device at room temperature and for delivery of the device to the treatment site in the body. A second temporary shape may be also be desired, e.g., for storage of the device at cold temperature.

Accordingly, in some embodiments, the biodegradable copolymer of the invention comprises a third segment. In an embodiment, optionally in combination with one or more other embodiments described herein, the copolymer further comprises a third segment A', wherein the A' segment:

is made from at least one diisocyanate and at least one diol, diamine or dithiol chain extender;

has an $M_n$ from about 0.4 kDa to about 500 kDa;

may be attached to the B segment or the A segment; and may be the same as or different than the A segment.

The description herein, including the various embodiments, relating to the A segment may also apply to the A' segment, as appropriate. For example, in one embodiment, optionally in combination with one or more other embodiments described herein, the A' segment is made from one to four different polycondensation reactions involving a diisocyanate and a diol, diamine or dithiol chain extender, wherein each polycondensation reaction:

occurs from about 5 to about 5,000 times, and involves a diisocyanate and a diol, diamine or dithiol chain extender that may be the same as or different than any other diisocyanate(s) and any other diol, diamine or dithiol chain extender(s) involved in any other polycondensation reaction(s).

The A' segment may be attached to the B segment or the A segment. In an embodiment, the A' segment is attached to the B segment. In another embodiment, the A' segment is attached to the A segment.

Further, the A' segment may be the same as or different than the A segment. In one embodiment, the A and A' segments are the same. In another embodiment, the A and A' segments are different.

The A' segment, rather than the B segment, may serve as the segment responsible for switching the polymeric composition to the permanent shape. Alternatively, the A' segment may be responsible for a second temporary shape for various reasons, e.g., for storage of the implantable device at cold temperature. Accordingly, in one embodiment, optionally in combination with one or more other embodiments described herein, the A' segment has a $T_g$ or $T_m$ in the range from about −70° C. to about 100° C. In narrower embodiments, the $T_g$ or $T_m$ of the A' segment is in the range from about −50° C. to about 80° C., or from about −30° C. to about 60° C., or from about −10° C. to about 40° C. In a particular embodiment, the A' segment has a $T_g$ or $T_m$ in the range from about −20° C. to about 35° C.

Although both the A and A' segments independently are made from at least one polycondensation reaction involving at least one diisocyanate and at least one diol, diamine or dithiol chain extender, they can possess different physical and mechanical properties. The physical and mechanical properties (e.g., the $T_g$ or $T_m$) of the A' segment can be tuned by appropriate selection of the diisocyanate(s) and chain extender(s) (including any functional groups in these compounds), the ratio and arrangement of the monomers within the segment, the length or molecular weight of the segment, and any other substance(s) chemically or non-chemically incorporated with the segment.

Biocompatible Polymer

Another embodiment of the invention, optionally in combination with one or more other embodiments described herein, is drawn to a composition comprising a biodegradable copolymer of the invention and at least one additional biologically compatible (or "biocompatible") polymer. The biocompatible polymer provides the inventive copolymer with biological, e.g., blood, compatibility. The at least one additional biocompatible polymer can be biodegradable or nondegradable. In an embodiment, the biocompatible polymer is biodegradable. The at least one additional biocompatible polymer can be selected in such a way as to make the entire inventive copolymer biologically degradable. In another embodiment, the biocompatible polymer is nondegradable. Moreover, the at least one additional biocompatible polymer may be blended, grafted, co-polymerized or incorporated with the polymers of the A and/or B segments (or any additional segments).

Examples of suitable biocompatible polymers include, but are not limited to, poly(ester amides), ethylene vinyl alcohol copolymer (commonly known by the generic name EVOH or by the trade name EVAL), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(D,L-lactide-co-glycolide) (PDLLAGA), poly(glycolic acid-co-trimethylene carbonate), polyphosphoesters, polyphosphoester urethanes, poly(amino acids), polycyanoacrylates, poly(trimethylene carbonate), poly(iminocarbonates), polyurethanes, polyphosphazenes, silicones, polyesters, polyolefins, polyisobutylene and ethylene-α-olefin copolymers, acrylic polymers and copolymers, vinyl halide polymers and copolymers (e.g., polyvinyl chloride), polyvinyl ethers (e.g., polyvinyl methyl ether), polyvinylidene halides (e.g., vinylidene fluoride based home or copolymer under the trade name Solef™ or Kynar™, e.g., polyvinylidene fluoride (PVDF) or poly(vinylidene-co-hexafluoropropylene) (PVDF-co-HFP) and polyvinylidene chloride), polyacrylonitrile, polyvinyl ketones, polyvinyl aromatics (e.g., polystyrene), polyvinyl esters (e.g., polyvinyl acetate), copolymers of vinyl monomers with each other and olefins (e.g., ethylene-methyl methacrylate copolymers, acrylonitrile-styrene copolymers, ABS resins, and ethylene-vinyl acetate copolymers), polyamides (e.g., Nylon 66 and polycaprolactam), alkyd resins, polycarbonates, polyoxymethylenes, polyimides, polyethers, poly(glyceryl sebacate), poly(propylene fumarate), epoxy resins, polyurethanes, rayon, rayon-triacetate, poly(N-acetylglucosamine) (Chitin), Chitosan, biomolecules (e.g., fibrin, fibrinogen, cellulose, starch, collagen and hyaluronic acid), cellulose derivatives (e.g., cellulose acetate, cellulose butyrate, cellulose acetate butyrate, cellophane, cellulose nitrate, cellulose propionate, cellulose ethers and carboxymethyl cellulose), and combinations and copolymers thereof.

In certain embodiments, optionally in combination with one or more other embodiments described herein, the at least one additional biocompatible polymer is selected from poly(ethylene glycol) (PEG); polypropylene; poly(propylene glycol) (PPG); poly(N-vinyl pyrrolidone) (PVP); poly(N-vinyl pyrrolidone-co-vinyl acetate) (Copovidone); poly(ester amides) (PEA); acrylic acid (AA); polyacrylates (e.g., poly(methyl methacrylate) (PMMA), poly(butyl methacrylate), poly(ethyl methacrylate), hydroxyethylmethacrylate (HEMA), poly(ethyl methacrylate-co-butyl methacrylate) (P(MMA-co BMA)), ethyl glycol dimethacrylate, (EGDMA), and ethylene-methyl methacrylate copolymers); acrylamides (e.g., N,N-dimethyl acrylamide, diacetone acrylamide, and acrylamide-methyl-propane sulfonate (AMPS)); fluorinated polymers or copolymers (e.g., poly(vinylidene fluoride) and poly(vinylidene fluoride-co-hexafluoro propene)); poly(hydroxyvalerate); poly(L-lactic acid)/polylactide (PLLA); poly(ε-caprolactone); poly(lactide-co-glycolide) (PLGA); poly(hydroxybutyrate); poly(hydroxyvalerate); poly(hydroxybutyrate-co-valerate); polydioxanone; polyorthoesters; polyanhydrides; poly(glycolic acid)/polyglycolide (PGA); poly(D,L-lactic acid) (PLA); poly(glycolic acid-co-trimethylene carbonate); polyphosphoesters; polyurethanes (e.g., polyphosphoester urethanes); polyureas; polyurethane(ureas); poly(amino acids); cyanoacrylates; poly(trimethylene carbonate); poly(iminocarbonates); co-poly(ether-esters) (e.g., PEO/PLA); polyalkylene oxalates; polyphosphazenes; silicones; polyesters; polyolefins; polyisobutylene and ethylene-α-olefin copolymers; vinyl halide polymers and copolymers (e.g., polyvinyl chloride (PVC)); polyvinyl ethers (e.g., polyvinyl methyl ether); polyvinylidene chloride; polyacrylonitrile; polyvinyl ketones; polyvinyl aromatics (e.g., polystyrene, styrene sulfonate, and acrylonitrile-styrene copolymers); polyvinyl esters (e.g., polyvinyl acetate); copolymers of vinyl monomers with each other (e.g., divinyl benzene (PVB)); olefins (e.g., poly(ethylene-co-vinyl alcohol) (EVAL)); poly(vinyl alcohol) (PVA); acrylonitrile butadiene (ABS) resins; ethylene-vinyl acetate copolymers; polyamides (e.g., Nylon 66 and polycaprolactam); alkyl resins; polycarbonates; polyoxymethylenes; polyimides; polyethers; epoxy resins; rayon; rayon-triacetate; and combinations and co-polymers thereof.

In another embodiment, optionally in combination with one or more other embodiments described herein, the at least one additional biocompatible polymer includes at least one polyester. Non-limiting examples of suitable polyesters include PLA, PLGA, PGA, PHA, poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), and polycaprolactone (PCL).

In some embodiments, optionally in combination with one or more other embodiments described herein, the at least one additional biocompatible polymer specifically cannot be one or more of any of the biocompatible polymers described herein.

The molecular weight of the at least one additional biocompatible polymer may be chosen to be 40 kDa or less to ensure renal clearance of the compound, e.g., between about 300 and about 40,000 Daltons, or between about 8,000 and about 30,000 Daltons (e.g., about 15,000 Daltons).

The biocompatible polymer can provide a controlled release of a bioactive agent, if incorporated with a polymeric material of which an implantable device is formed. Controlled release and delivery of a bioactive agent using a polymeric carrier has been extensively researched. See, e.g., Mathiowitz, Ed., Encyclopedia of Controlled Drug Delivery, C.H.I.P.S. (1999). The release rate of the bioactive agent can be controlled by various means, e.g., selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. One of ordinary skill in the art can readily select a carrier system using a biocompatible polymer to provide a controlled release of the bioactive agent.

Biobeneficial Materials

A further embodiment of the invention, optionally in combination with one or more other embodiments described herein, is directed to a composition comprising a biodegradable copolymer of the invention and at least one biobeneficial material. The biobeneficial material may be a polymeric material or a non-polymeric material, and may be biodegradable or non-degradable. In certain embodiments, the at least one biobeneficial material is flexible, biodegradable, biocompatible, non-toxic, non-antigenic and/or non-immunogenic. The biobeneficial material may be blended, grafted, co-polymerized or incorporated with the polymers of the A and/or B segments (or any additional segments).

The biobeneficial material, if polymeric, may have a relatively low $T_g$, e.g., a $T_g$ below or significantly below that of the biocompatible polymer. In an embodiment, the $T_g$ of the biobeneficial material is below body temperature. This attribute would, e.g., render the biobeneficial material relatively soft as compared to the biocompatible polymer and allow, e.g., a layer of coating containing the biobeneficial material to fill any surface damages that may arise with an implantable device coated with a layer comprising the biocompatible polymer. For example, during radial expansion of a stent, a more rigid biocompatible polymer can crack or have surface fractures. A softer biobeneficial material can fill in the crack and fractures.

The biobeneficial material may also be hydrophlic. Hydrophicility of, e.g., the coating material would affect the drug-release rate of a drug-delivery coating and, if the coating material is biodegradable, would affect the degradation rate of the coating material. Generally, the more hydrophilic the coating material, the greater the drug-release rate of the drug-delivery coating and the greater the degradation rate of the coating if it is biodegradable.

Examples of biobeneficial materials include, but are not limited to, polyethers (e.g., poly(ethylene glycol) (PEG)); poly(ether esters); co-poly(ether-esters) (e.g. PEO/PLA); polyalkylene oxides (e.g., poly(ethylene oxide) and polypropylene oxide)); polyalkylene oxalates; polyphosphazenes; phosphoryl choline; choline; poly(aspirin); polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and N-vinyl pyrrolidone (VP); carboxylic acid bearing monomers such as methacrylic acid (MA), acrylic acid (AA), alkoxymethacrylate, alkoxyacrylate, and 3-trimethylsilylpropyl methacrylate (TM-SPMA); copolymers of PEG such as poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), and poly(vinylidene fluoride)-PEG (PVDF-PEG); PLURONICTM surfactants (polypropylene oxide-co-polyethylene glycol); poly(tetramethylene glycol); biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharides, elastin, chitosan, and alginate; silicones; and combinations and copolymers thereof.

In certain embodiments, optionally in combination with one or more other embodiments described herein, the at least one biobeneficial material is selected from fibrin; fibrinogen; cellulose and cellulose derivatives (e.g., cellulose acetate, cellulose butyrate, cellulose acetate butyrate, cellophane, cellulose nitrate, cellulose propionate, cellulose ethers, and carboxymethyl cellulose); starch; pectin; chitosan; elastin; gelatin; alginate and conjugates thereof (e.g., alginate-gelatin, alginate-collagen, alginate-laminin, alginate-elastin, alginate-collagen-laminin and alginate-hyaluronic acid); collagen and conjugates thereof; hyaluronan and derivatives thereof (e.g., methacrylate-modified hyaluronan and NHS ester-modified hyaluronan); hyaluronic acid; sodium hyaluronate; and self-assembled peptides (SAP) (e.g., AcN-RARADADARARADADA-CNH$_2$ (RAD 16-II), VKVKVKVKV-PP-TKVKVKVKV-NH$_2$ (MAX-1), and AcN-AEAEAKAKAEAEAKAK-CNH$_2$ (EAK 16-II)).

In another embodiment, the biobeneficial material is a block copolymer having flexible poly(ethylene glycol) and poly(butylene terephthalate) blocks (PEG/PBT) (e.g., Poly-Active™). PolyActive™ is intended to include AB, ABA, and BAB copolymers having such segments of PEG and PBT (e.g., poly(ethylene glycol)-block-poly(butylene terephthalate)-block-poly(ethylene glycol) (PEG-PBT-PEG)).

In some embodiments, optionally in combination with one or more other embodiments described herein, the at least one biobeneficial material specifically cannot be one or more of any of the biobeneficial materials described herein.

Biologically Active Agents

Another embodiment of the invention, optionally in combination with one or more other embodiments described herein, is directed to a composition comprising a biodegradable copolymer of the invention and at least one biologically active (or "bioactive") agent. The at least one biologically active agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In an embodiment, optionally in combination with one or more other embodiments described herein, the inventive composition comprises at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin I$_1$, actinomycin X$_1$, and actinomycin C$_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent may be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammmatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that may also have cytostatic or antiproliferative properties include, but are not limited to, heparin, sodium heparin, low molecular weight heparins, heparinoids, hirudin, recombinant hirudin, thrombomodulin, flavonoids, salicylate (aspirin), argatroban, forskolin, vapiprost, prostacyclin and prostacyclin analogues, dextran, atrial natriuretic peptide (ANP), D-phe-pro-arg-chloromethylketone (synthetic antithrombin), dipyridamole, glycoprotein IIb/IIIa platelet membrane receptor antagonist antibody, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO).

Other bioactive agents can include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent may be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable. Moreover, useful bioactive agents include prodrugs and co-drugs of the agents and drugs described herein.

In a more specific embodiment, optionally in combination with one or more other embodiments described herein, the composition of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, bioactive RGD, CD-34 antibody, abciximab (REOPRO), progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

In some embodiments, optionally in combination with one or more other embodiments described herein, the at least one biologically active agent specifically cannot be one or more of any of the bioactive drugs or agents described herein.

The dosage or concentration of the at least one bioactive agent required to produce a favorable therapeutic effect should be less than the level at which the bioactive agent produces toxic effects and greater than the level at which non-therapeutic results are obtained. The dosage or concentration of the bioactive agent required to, e.g., inhibit the target cellular activity of the vascular region can depend upon various factors such as the particular circumstances of the patient, the nature of the trauma, the nature of the therapy desired, the time over which the administered agent resides at the vascular site, and if other active agents are employed, the nature and type of the substance or combination of substances. Therapeutically effective concentrations or dosages can be determined empirically, e.g., by infusing vessels from suitable animal model systems and using immunohistochemical, fluorescent or electron microscopy methods to detect the agent and its effects, or by conducting suitable in vitro studies. Standard pharmacological test procedures to determine concentrations or dosages are understood by one of ordinary skill in the art.

Material And Coating

The inventive composition comprising the biodegradable copolymer can be used to make a material of which an implantable device is formed. Such a material can comprise any combination of embodiments of the inventive composition described herein.

Accordingly, an embodiment of the invention, optionally in combination with one or more other embodiments described herein, is drawn to a material containing any combination of embodiments of the composition comprising the biodegradable copolymer. For example, the composition forming the material can optionally contain a third segment A', at least one non-fouling moiety, at least one additional biocompatible polymer, at least one biobeneficial material, at least one bioactive agent, or a combination thereof.

The material of the invention can be used to make a portion of an implantable device or the whole device itself. For example, the material can be used to make a coating that is disposed over at least a portion of an implantable device.

Accordingly, an embodiment of the invention, optionally in combination with one or more other embodiments described herein, is directed to a coating containing any combination of embodiments of the composition comprising the biodegradable copolymer. For example, the composition forming the coating can optionally contain a third segment A', at least one non-fouling moiety, at least one additional biocompatible polymer, at least one biobeneficial material, at least one bioactive agent, or a combination thereof.

The coating can have a range of thickness and biodegradation rates. In some embodiments, optionally in combination with one or more other embodiments described herein, the coating has a thickness of ≤about 30 micron, or ≤about 20 micron, or ≤about 10 micron. In a particular embodiment, the coating has a thickness of ≤about 10 micron. In further embodiments, optionally in combination with one or more other embodiments described herein, the coating completely or substantially completely degrades within about 24 months, or within about 18 months, or within about 12 months, or within about 6 months, or within about 3 months, or within about 2 months, or within about 1 month (i.e., 30 days). In a specific embodiment, the coating completely or substantially completely degrades within about 12 months.

Implantable Device

The inventive material containing any combination of embodiments of the composition comprising the biodegradable copolymer can be used to form an implantable device. Accordingly, one embodiment of the invention, optionally in combination with one or more other embodiments described herein, is directed to an implantable device formed of a material containing any combination of embodiments of the composition comprising the biodegradable copolymer. For example, the implantable device can be formed of a material comprising a composition that optionally contains a third segment A', at least one non-fouling moiety, at least one additional biocompatible polymer, at least one biobeneficial material, at least one bioactive agent, or a combination thereof.

A portion of the implantable device or the whole device itself can be formed of the material containing any combination of embodiments of the composition comprising the biodegradable copolymer. For example, at least a portion of the implantable device can be coated by a coating containing any combination of embodiments of the composition comprising the biodegradable copolymer.

Accordingly, an embodiment of the invention, optionally in combination with one or more other embodiments described herein, is directed to an implantable device formed of a coating containing any combination of embodiments of the composition comprising the biodegradable copolymer. For example, the implantable device can be formed of a coating comprising a composition that optionally contains a third segment A', at least one non-fouling moiety, at least one additional biocompatible polymer, at least one biobeneficial material, at least one bioactive agent, or a combination thereof.

The implantable device can be formed of a coating that can have a range of thickness and biodegradation rates. In some embodiments, optionally in combination with one or more other embodiments described herein, the implantable device is formed of a coating that has a thickness of ≤about 30 micron, or ≤about 20 micron, or ≤about 10 micron. In a particular embodiment, the device is formed of a coating that has a thickness of ≤about 10 micron. In further embodiments, optionally in combination with one or more other embodiments described herein, the implantable device is formed of a coating that completely or substantially completely degrades within about 24 months, or within about 18 months, or within about 12 months, or within about 6 months, or within about 3 months, or within about 2 months, or within about 1 month (i.e., 30 days). In a specific embodiment, the device is formed of a coating that completely or substantially completely degrades within about 12 months.

The present invention also encompasses implantable devices formed of bioabsorbable and/or biostable polymers. In some embodiments, optionally in combination with one or more other embodiments described herein, a portion of the device (e.g., a coating disposed over the device) or the whole device itself can be formed of such polymers and any other substances described herein.

Any implantable device can be formed of the inventive material containing any combination of embodiments of the composition comprising the biodegradable copolymer. Examples of implantable devices include, but are not limited to, stents (e.g., coronary stents and peripheral stents), grafts (e.g., aortic grafts, arterio-venous grafts, vascular grafts and by-pass grafts), stent-grafts, catheters, guidewires, leads and electrodes for pacemakers and defibrillators, endocardial leads (e.g., FINELINE and ENDOTAK, available from Abbott Vascular, Santa Clara, Calif.), clips (e.g., anastomotic clips), shunts (e.g., cerebrospinal fluid and axius coronary shunts), closure devices (e.g., arterial and patent foramen ovale closure devices), valves (e.g., artificial heart valves), ventricular assist devices, artificial heart, and blood oxygenators. Furthermore, the inventive material containing any combination of embodiments of the composition comprising the biodegradable copolymer can be used to make other types of substrates including, e.g., sustained-release small molecule or protein formulations, microspheres and nanofibers.

In an embodiment, optionally in combination with one or more other embodiments described herein, the implantable device is selected from stents, grafts, stent-grafts, catheters, leads and electrodes, clips, shunts, closure devices, and valves. In a more specific embodiment, optionally in combination with one or more other embodiments described herein, the implantable device is a stent. The stent may be balloon-expandable or self-expandable. Moreover, the stent can be intended for any vessel in the body, e.g., neurological, carotid, vein graft, coronary, aortic renal, iliac, femoral, popliteal vasculature and urethral passages.

The underlying structure of the implantable device can be of virtually any design. A portion of the device, or the whole device itself, can be made of a metallic material, an alloy, a polymeric material, any other type of material, or a combination thereof, as is known in the art. For example, a polymeric material comprising any combination of embodiments of the inventive composition can be used to make a portion of the implantable device or the whole device itself.

Non-limiting examples of metallic materials and alloys suitable for fabricating implantable devices include cobalt-chromium alloys (e.g., ELGILOY), "L-605", stainless steel (316L), "MP35N," "MP20N," ELASTINITE (Nitinol), tantalum, tantalum-based alloys, nickel-titanium alloys, platinum, platinum-based alloys (e.g., platinum-iridium alloy), iridium, gold, magnesium, titanium, titanium-based alloys, zirconium-based alloys, or combinations thereof. "L-605" is a trade name for an alloy of cobalt, chromium, tungsten, nickel and iron available as Haynes 25 from Haynes International (Kokomo, Ind.). "L-605" consists of 51% cobalt, 20% chromium, 15% tungsten, 10% nickel and 3% iron. "MP35N" and "MP20N" are trade names for alloys of cobalt, nickel, chromium and molybdenum available from Standard Press Steel Co. (Jenkintown, Pa.). "MP35N" consists of 35% cobalt, 35% nickel, 20% chromium and 10% molybdenum. "MP20N" consists of 50% cobalt, 20% nickel, 20% chromium and 10% molybdenum.

If a polymeric material is used to make a portion (e.g., a coating) of the implantable device or the whole device itself, the polymeric material can comprise any combination of embodiments of the inventive composition, e.g., the biodegradable copolymer of the invention, a blend of different types of polymers, a blend of polymer(s) and additional substance(s), or a combination thereof. Further, additional polymer(s) and/or additional substance(s) can be attached to the underlying copolymer forming the device or a portion thereof. The additional polymer(s) and/or additional substance(s) that may be attached to, grafted to, blended with, co-polymerized with, or incorporated with the underlying polymer can include, but are not limited to, biocompatible polymers, bioabsorbable polymers, biocompatible moieties, non-fouling moieties, biobeneficial substances and materials, and bioactive agents. To enhance the mechanical characteristics (e.g., strength and rigidity) of an implantable device made substantially of a polymeric material, the device can be supported by additional structure(s) (e.g., struts in the case of stents made substantially of a polymeric material).

Structure of Coating

According to some embodiments of the invention, optionally in combination with one or more other embodiments described herein, a coating disposed over an implantable device (e.g., a stent) can be a multi-layer structure that can include any of the following four layers or combination thereof:

(1) a primer layer;
(2) a drug-polymer layer (also referred to as a "reservoir" or "reservoir layer") or, alternatively, a polymer-free drug layer;
(3) a topcoat layer; and/or
(4) a finishing coat layer.

Each layer of a stent coating can be disposed over the stent by dissolving the polymer or a blend of polymers in a solvent, or a mixture of solvents, and disposing the resulting polymer solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to improve the thermodynamic stability of the coating.

To incorporate a bioactive agent (e.g., a drug) into the reservoir layer, the drug can be combined with the polymer solution that is disposed over the stent as described above. Alternatively, if it is desirable to have the stent coating with a fast drug-release rate, a polymer-free reservoir can be made. To fabricate a polymer-free reservoir, the drug can be dissolved in a suitable solvent or mixture of solvents, and the resulting drug solution can be disposed over the stent by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied directly or indirectly over at least a portion of the stent surface to serve as a reservoir for at least one bioactive agent (e.g., drug) that is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through non-degradable polymeric layer(s) into a blood vessel or tissue.

In one embodiment, any or all of the layers of the stent coating can be made of biologically degradable/erodable/absorbable/resorbable polymer(s), non-degradable/biostable polymer(s), or a combination thereof. In another embodiment, the outermost layer of the coating can be limited to biodegradable polymer(s), biostable polymer(s), or a combination thereof.

To illustrate in more detail, in a stent coating having all four layers described above (i.e., the primer, the reservoir layer, the topcoat layer and the finishing coat layer), the outermost layer is the finishing coat layer, which can be made of biodegradable polymer(s), biostable polymer(s), or a combination thereof. The remaining layers (i.e., the primer, the reservoir layer and the topcoat layer) optionally can also be fabricated of biodegradable polymer(s), biostable polymer(s), or a combination thereof. The polymer(s) in a particular layer may be the same as or different than those in any of the other layers.

If a finishing coat layer is not used, the topcoat layer can be the outermost layer and can be made of biodegradable polymer(s), biostable polymer(s), or a combination thereof. In this case, the remaining layers (i.e., the primer and the reservoir layer) optionally can also be fabricated of biodegradable polymer(s), biostable polymer(s), or a combination thereof. The polymer(s) in a particular layer may be the same as or different than those in any of the other layers.

If neither a finishing coat layer nor a topcoat layer is used, the stent coating could have only two layers—the primer and the reservoir. In such a case, the reservoir is the outermost layer of the stent coating and can be made of biodegradable polymer(s), biostable polymer(s), or a combination thereof. The primer optionally can also be fabricated of biodegradable polymer(s), biostable polymer(s), or a combination thereof. The two layers may be made from the same or different polymers.

Increased rate of degradation, erosion, absorption and/or resorption of biologically degradable, erodable, absorbable and/or resorbable polymer(s) can lead to an increased rate of release of a drug due to the gradual disappearance of the polymer(s) that form the reservoir, the topcoat layer, and/or the finishing coat layer. Through appropriate selection of biodegradable polymer(s), biostable polymer(s) or a combination thereof, a stent coating can be engineered to provide either fast or slow release of a drug, as desired. Those having ordinary skill in the art can determine whether a stent coating having slow or fast drug-release rate is advisable for a particular drug. For example, fast release may be recommended for stent coatings loaded with antimigratory drugs, which often need to be released within 1 to 2 weeks. For antiproliferative and anti-inflammatory drugs, slower release may be desired, e.g., up to 30-day and 60-day release times, respectively.

Any layer of a stent coating can contain any amount of a bioabsorbable polymer and/or a biocompatible polymer, or a blend of more than one such polymer. Non-limiting examples of bioabsorbable polymers and biocompatible polymers include polyacrylates, e.g., poly(butyl methacrylate), poly (ethyl methacrylate), poly(ethyl methacrylate-co-butyl methacrylate), poly(acrylonitrile), poly(ethylene-co-methyl methacrylate), poly(acrylonitrile-co-styrene) and poly (cyanoacrylates); fluorinated polymers and/or copolymers, e.g., poly(vinylidene fluoride) and poly(vinylidene fluoride-co-hexafluoro propylene); poly(N-vinyl pyrrolidone) (PVP); poly(N-vinyl pyrrolidone-co-vinyl acetate) (Copovidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose); polyurethanes; silicones; polyesters; polyolefins; polyisobutylene and ethylene-alphaolefin copolymers; vinyl halide polymers and copolymers, e.g., polyvinyl chloride; polyvinyl ethers, e.g., polyvinyl methyl ether; polyvinylidene chloride; polyvinyl ketones; polyvinyl aromatics, e.g., polystyrene; polyvinyl esters, e.g., polyvinyl acetate; copolymers of vinyl monomers with each other and olefins, e.g., poly(ethylene-co-vinyl alcohol) (EVAL); ABS resins; poly(ethylene-co-vinyl acetate); polyamides, e.g., Nylon 66 and polycaprolactam; alkyd resins; polycarbonates; polyoxymethylenes; polyimides; polyethers, epoxy resins; polyurethanes; rayon; rayon-triacetate; and copolymers thereof.

Any layer of a stent coating can also contain any amount of a non-degradable polymer, or a blend of more than one such polymer. Non-limiting examples of non-degradable polymers include methylmethacrylate, ethylmethacrylate, butylmethacrylate, 2-ethylhexylmethacrylate, laurylmethacrylate, hydroxyl ethyl methacrylate, polyethylene glycol (PEG) acrylate, PEG methacrylate, 2-methacryloyloxyethylphosphorylcholine (MPC) and N-vinyl pyrrolidone, methacrylic acid, acrylic acid, hydroxypropyl methacrylate, hydroxypropylmethacrylamide, 3-trimethylsilylpropyl methacrylate, and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing any combination of embodiments of the composition comprising the biodegradable copolymer. For example, the method comprises forming the implantable device of a material comprising a composition that optionally contains a third segment A', at least one non-fouling moiety, at least one additional biocompatible polymer, at least one biobeneficial material, at least one bioactive agent, or a combination thereof.

Under the method, a portion of the implantable device or the whole device itself can be formed of the material containing any combination of embodiments of the composition comprising the biodegradable copolymer. Moreover, the method can comprise depositing, or disposing, over at least a portion of the implantable device a coating containing any combination of embodiments of the composition comprising the biodegradable copolymer.

Accordingly, in an embodiment, the method comprises disposing over at least a portion of an implantable device a coating containing any combination of embodiments of the composition comprising the biodegradable copolymer. For example, the method comprises disposing over at least a portion of an implantable device a coating comprising a composition that optionally contains a third segment A', at least one non-fouling moiety, at least one additional biocompatible polymer, at least one biobeneficial material, at least one bioactive agent, or a combination thereof. The coating can be disposed over the implantable device by any of various methods known in the art, such as dip coat, syringe drip coat, spray coat, etc.

The method of the invention can deposit a coating having a range of thickness over an implantable device. In certain embodiments, the method deposits over at least a portion of the implantable device a coating that has a thickness of ≤about 30 micron, or ≤about 20 micron, or ≤about 10 micron. In a particular embodiment, the method deposits a coating that has a thickness of ≤about 10 micron.

According to an embodiment, the method is used to fabricate an implantable device selected from stents, grafts, stent-grafts, catheters, leads and electrodes, clips, shunts, closure devices, and valves. In a specific embodiment, the method is used to fabricate a stent.

In general, representative examples of polymers that can be used to fabricate an implantable device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide), poly(D,L-lactide), poly(caprolactone), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be well suited for fabricating an implantable device include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from ATOFINA Chemicals of Philadelphia, Pa.), poly(tetrafluoroethylene-co-hexafluoropropylene-co-vinylidene fluoride), ethylene-vinyl acetate copolymers, and polyethylene glycol.

The copolymer of the invention, and any other desired substances and materials, can be formed into a polymer construct, such as a tube or sheet that can be rolled or bonded to form a construct such as a tube. A tube can be formed from melt extrusion of the copolymer or from wet extrusion of the copolymer in a solvent conventionally, by electrospinning, or by other methods such as thermally induced phase separation.

An implantable device can then be fabricated from the polymer construct. For example, a stent can be fabricated from a tube by laser machining a pattern into the tube. In another embodiment, the polymer construct can be formed from the polymeric material of the invention using an injection-molding apparatus.

In an exemplary method of fabricating an implantable device possessing shape-memory properties, polymeric tubes of the inventive copolymer are extruded or processed from the melt and elongated to the desired final dimensions (e.g., diameter) of the device at a temperature at or above the $T_g$ or $T_m$ of the harder A segment. The tubes are then cooled to a temperature below the $T_g$ or $T_m$ of the A segment while being held at the final implant dimensions, and laser cut to create the design of the implant (e.g., a stent). Next, the stent is heated to a temperature at or above the $T_g$ or $T_m$ of the softer B segment, crimped to the delivery size (the temporary shape), and then cooled to a temperature below the $T_g$ or $T_m$ of the B segment while being held at the delivery size. The stent can also be inserted in a sheath or a sock and then sterilized at elevated temperature (e.g., 40-45° C.), which avoids recovering the permanent shape of the stent even if the transition temperature is around body temperature.

Method of Treating Or Preventing Disorders

An implantable device formed of a material containing any combination of embodiments of the composition comprising the biodegradable copolymer can be used to treat, prevent or diagnose a variety of conditions or disorders. The material can form a portion of the device (e.g., a coating disposed over the device) or the whole device. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction.

An implantable device formed of a material comprising the inventive copolymer is particularly suitable for the treatment or prevention of conditions or disorders that are sensitive to high pressure. For example, use of the inventive device displaying shape-memory effects avoids the high pressure associated with the inflation of a balloon during the deployment of a balloon-expandable stent. The high pressure associated with balloon-expansion of a stent could potentially rupture a vulnerable plaque, causing formation of a blood clot that could completely block an artery and result in adverse coronary events such as a heart attack.

Accordingly, an embodiment of the invention, optionally in combination with one or more other embodiments described herein, is drawn to a method of treating, preventing or diagnosing a condition or disorder in a patient, comprising implanting in the patient an implantable device formed of a material containing any combination of embodiments of the composition comprising the biodegradable copolymer. For example, the implantable device can be formed of a material comprising a composition that optionally contains a third segment A', at least one non-fouling moiety, at least one additional biocompatible polymer, at least one biobeneficial material, at least one bioactive agent, or a combination thereof. A portion of the device, or the whole device itself, can be formed of the inventive material. Moreover, the material can be a coating disposed over the device.

In an embodiment, the condition or disorder treated, prevented or diagnosed by the implantable device is selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a more specific embodiment, the condition or disorder is selected from atherosclerosis, thrombosis, restenosis and vulnerable plaque.

In one embodiment, the implantable device employed in the method is formed of a material containing at least one biologically active agent selected from antiproliferative, antineoplastic, anti-inflammatory, antiplatelet, anticoagulant, antifibrin, antithrombin, antimitotic, antibiotic, antiallergic and antioxidant substances. In a more specific embodiment, the at least one bioactive agent is selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, bioactive RGD, CD-34 antibody, abciximab (REOPRO), progenitor cell-capturing antibodies, prohealing drugs, prodrugs thereof, co-drugs thereof, and a combination thereof.

In some embodiments, the at least one biologically active agent delivered by the implantable device specifically cannot be one or more of any of the bioactive drugs or agents described herein.

In an embodiment, the implantable device used in the method is selected from stents, grafts, stent-grafts, catheters, leads and electrodes, clips, shunts, closure devices, and valves. In a specific embodiment, the implantable device is a stent.

After delivery of the device (e.g., a stent) to the treatment site in the body, deployment of the device under physiological conditions, including provision of a thermal stimulus to the device if the transition temperature of the polymeric composition is above body temperature, leads to recovery of the permanent shape of the device (its initial extruded size). As an example, exposure of a stent to a temperature at or above the transition temperature triggers the self-expansion of the stent to a diameter appropriate for the target vessel.

If the B segment is the switching segment and has a $T_g$ or $T_m$ greater than body temperature, then a thermal stimulus would be needed to trigger the recovery of the permanent shape of the implantable device formed of the inventive polymeric composition. In such cases, the method of treatment or prevention further comprises providing a thermal stimulus to the implantable device such that the temperature of the composition is at or above the $T_g$ or $T_m$ of the B segment but below the $T_g$ or $T_m$ of the A segment.

The thermal stimulus can be provided by any of various sources and means known in the art, e.g., by laser, ultrasonic wave, high frequency wave, infrared radiation, hot air stream or hot water. In a particular embodiment, the thermal stimulus is provided by a catheter. For example, a catheter attached to a stent and containing a suitable thermal stimulus within its lumen or other internal compartment can provide the thermal stimulus to the stent after the stent is delivered to the treatment site. When deployed or unsheathed upon removal of the stress maintaining the stent's compact, temporary shape, the stent can recover immediately to the desired permanent shape.

As explained earlier, a thermal stimulus can be provided safely within a short period of time (e.g., within several seconds) or by appropriate thermal shielding of the implantable device or another article that delivers the device and provides the thermal stimulus. For example, a stent can be delivered through a catheter that contains an outer insulating or cooling component to shield the blood and tissues from the catheter compartment providing the thermal stimulus.

Synthesis of Copolymers of Invention

The biodegradable copolymers of the invention can be prepared by any method of polymerization known in the art. Methods of polymerization include, but are not limited to, solution-based polymerization and melt-phase polymerization. In solution-based polymerization, all the reactive components involved in the polymerization reaction are dissolved in a solvent.

The copolymers of the invention can be synthesized in bulk or in solution through polycondensation of a hydroxyl-, amino- or thiol-containing polymer (the B segment) with one or more diisocyanates and one or more diol, diamine and/or dithiol chain extenders to form the A segment (and the A' segment, if desired). The reaction may be one-step, with all components added, or multi-step. A traditional approach is two-step, wherein the hydroxyl-, amino- or thiol-containing B segment polymer first reacts with a diisocyanate, followed by chain extension upon addition of a diol, diamine or dithiol chain extender.

The polycondensation reaction can be catalyzed by an organic or inorganic acid (e.g., a Lewis acid), an organic (e.g., a tertiary amine base) or inorganic base (e.g., a Lewis base), an organometallic reagent, and/or heat, if necessary and if compatible with the reactants and product(s) of the reaction. Typical catalysts are Lewis acid salts and tertiary amines. Tin catalysts (e.g., stannous octoate and tin triflates) are particularly suitable for use with aliphatic diisocyanates.

The inventive copolymers can be synthesized various ways, as is known in the art. For example, the A segment can be generated as a block by repeating a polycondensation reaction of a particular diisocyanate and a particular diol, diamine or dithiol chain extender a desired number of times, optionally performing another polycondensation reaction of another diisocyanate and another diol, diamine or dithiol chain extender a desired number of times, and so on. The A segment can also be synthesized as an alternating copolymer by alternating the various polycondensation reactions as desired. Moreover, the A segment can be synthesized in a random fashion by conducting a polycondensation reaction involving at least two different diisocyanates and a particular chain extender, or a particular diisocyanate and at least two different chain extenders, or at least two different diisocyanates and at least two different chain extenders in the same pot, and optionally performing other polycondensation reaction(s) involving different diisocyanate(s) and/or different chain extender(s) in the same pot. The mechanical properties (e.g., strength, rigidity, toughness, flexibility, deformation and recovery) and physical properties (e.g., $T_g$ or $T_m$, the temperature range of the thermal transitions, degradation rate and drug-release rate) of the copolymer can all vary based on the amount of randomness.

One method of preparing an AB disegment copolymer is to conduct polycondensation of a diisocyanate and a diol, diamine or dithiol chain extender with a B segment polymer containing at least one hydroxyl, amino or thiol end group, and optionally performing additional polycondensation reaction(s) with additional diisocyanate(s) and additional diol, diamine or dithiol chain extender(s), wherein the same or different diisocyanates and chain extenders may be employed in the various polycondensation reactions. The same procedure can be used to synthesize an ABA' trisegment copolymer in which the same A and A' segments are copolymerized with a B segment polymer containing two hydroxyl, amino or thiol end groups.

Likewise, an A-B-A' trisegment copolymer, in which the A and A' segments are different, can be synthesized by:
performing polycondensation of a diisocyanate and a diol, diamine or dithiol chain extender with a B segment polymer containing a free hydroxyl, amino or thiol end group and a protected hydroxyl, amino or thiol end group;
optionally performing additional polycondensation reaction(s) with additional diisocyanate(s) and additional diol, diamine or dithiol chain extender(s);
protecting the functional group formed at the polymer end of the A segment;
deprotecting the protected hydroxyl, amino or thiol end group of the B segment;
performing polycondensation of a diisocyanate and a diol, diamine or dithiol chain extender with the deprotected hydroxyl, amino or thiol end group of the B segment;
optionally performing additional polycondensation reaction(s) with additional diisocyanate(s) and additional diol, diamine or dithiol chain extender(s); and
optionally deprotecting the protected functional group at the polymer end of the A segment.

The same or different diisocyanates and chain extenders may be employed in the various polycondensation reactions to make the A and/or A' segments. A similar procedure can be used to synthesize an A'-A-B trisegment copolymer, except that the polycondensation reaction(s) to make the A' segment are initiated with the functional group formed at the polymer end of the A segment and the protected end group of the B segment remains protected during the formation of the A' segment.

Various embodiments of the inventive composition comprising a biodegradable copolymer can be prepared by optionally:
conjugating at least one dihydroxyaryl group to the polymer ends of the copolymer;
blending or attaching at least one non-fouling moiety with or to the copolymer;
blending or attaching at least one additional biocompatible polymer with or to the copolymer;
blending or attaching at least one biobeneficial material with or to the copolymer; and/or
incorporating at least one biologically active agent.

The at least one dihydroxyaryl group conjugated to the polymer ends can contain, e.g., an ortho-dihydroxyphenyl moiety such as 1,2-dihydroxyphenyl and 3,4-dihydroxyphenyl. 3,4-Dihydroxyphenyl-containing compounds include, e.g., dopamine and 3,4-dihydroxyhydrocinnamic acid. Dopamine could be conjugated to, e.g., hydroxyl end groups of a copolymer via coupling with 1,1'-carbonyldiimidazole. 3,4-Dihydroxy-hydrocinnamic acid could be conjugated to hydroxyl end groups by conversion of the cinnamic acid to the N-succidimyl ester or by use of dicyclohexylcarbodiimide (DCC) and 4-(dimethylamino)pyridinium (DPTS). Alternatively, conjugation of the innamic acid could be effected via a Mitsunobu reaction using triphenylphosphine and diethyl azodicarboxylate (DEAD) or diisopropyl azodicarboxylate (DIAD). Conjugation of a dihydroxyaryl group to an active end group (e.g., a hydroxyl, amino or thiol group) could also be effected using other reagents and methods, as is known in the art.

Manufacture of Implantable Device Displaying Shape-Memory Effects

If an article (e.g., an implantable device) is formed of a two-segment copolymer possessing shape-memory properties, the permanent shape of the article can be created by:
(1) heating the article to a temperature at or above the $T_g$ or $T_m$ of the "harder" segment into a melt;
(2) mechanically stressing and melt-molding the article into the desired permanent shape at the elevated temperature; and then
(3) cooling the article below the $T_g$ or $T_m$ of the harder segment while the article remains under stress and held in the permanent shape.

Similarly, the temporary shape of the article can be formed by:
(1) heating the article to a temperature at or above the $T_g$ or $T_m$ of the "softer" segment, but below the $T_g$ or $T_m$ of the harder segment, to fluidize the softer segment;
(2) mechanically stressing and molding the article into the desired temporary shape at the elevated temperature; and then
(3) cooling the article below the $T_g$ or $T_m$ of the softer segment while the article remains under stress and held in the temporary shape.

If the article is formed of a shape-memory copolymer containing three segments, the article can have one permanent shape and two temporary shapes. The third, "softest" segment would be responsible for a second temporary shape. Likewise, the second temporary shape of the article can be formed by:
(1) heating the article to a temperature at or above the $T_g$ or $T_m$ of the softest segment, but below the $T_g$ or $T_m$ of the softer segment, to fluidize the softest segment;
(2) mechanically stressing and molding the article into the desired second temporary shape at the elevated temperature; and then
(3) cooling the article below the $T_g$ or $T$ of the softest segment while the article remains under stress and held in the second temporary shape.

Other methods can be used to form the permanent shape or the temporary shape(s) of the article. For example, the permanent shape of the article can also be created by heating or forming a pre-polymer solution to the desired permanent shape and then covalently crosslinking while the article remains under stress to hold the permanent shape.

As another example, the permanent shape or the temporary shape(s) of the article can be created via a solvent extrusion method by:
(1) dissolving the article in a solvent or a mixture of solvents, evaporating off the solvent(s), and heating the article to a temperature at or above the $T_g$ or $T_m$ of the harder segment (to create the permanent shape) or the softer segment (to create the temporary shape);
(2) mechanically stressing and molding the article into the desired permanent shape or temporary shape at the elevated temperature; and then
(3) cooling the article below the $T_g$ or $T_m$ of the harder segment or the softer segment while the article remains under stress and held in the permanent shape or the temporary shape.

While particular embodiments of the present invention have been shown and described, it will be obvious to those skilled in the art that changes and modifications can be made thereto without departing from the invention in its broader aspects. Therefore, the appended claims are to encompass within their scope all such changes and modifications as fall within the true spirit and scope of the present invention.

What is claimed is:

1. A composition comprising a biodegradable copolymer comprising at least two segments A and B, wherein:
the A segment has a $T_g$ or $T_m$ in the range from about 50° C. to about 300° C. and is made from at least one diisocyanate and at least one diol, diamine or dithiol chain extender;
the B segment has a $T_g$ or $T_m$ in the range from about 30° C. to about 100° C. and is derived from a polymer containing at least one hydroxyl, amino or thiol end group;
the $T_g$ or $T_m$ of the A segment is at least about 20° C. greater than the $T_g$ or $T_m$ of the B segment;
the A and B segments each independently have a polymer number-average molecular weight ($M_n$) from about 0.4, kDa to about 500, kDa;
and wherein:
the composition displays at least one shape-memory effect, and
a permanent shape of the composition is obtained when the temperature of the composition is equal to or greater than the $T_g$ or $T_m$ of the B segment;
wherein at least one dihydroxyaryl group is conjugated to the end(s) of the copolymer.

2. The composition of claim 1, wherein the A segment has a $T_g$ or $T_m$ in the range from about 70° C. to about 260° C. and the B segment has a $T_g$ or $T_m$ in the range from about 35° C. to about 70° C.

3. The composition of claim 2, wherein the $T_g$ or $T_m$ of the B segment is in the range from about 35° C. to about 40° C.

4. The composition of claim 1, wherein the $T_g$ or $T_m$ of the A segment is at least about 40° C. greater than the $T_g$ or $T_m$ of the B segment.

5. The composition of claim 1, wherein the B segment is derived from a polymer comprising from one to four different types of monomer, wherein each type of monomer has from about 5, to about 5,000, monomer units.

6. The composition of claim 1, wherein the A segment is made from one to four different polycondensation reactions involving a diisocyanate and a diol, diamine or dithiol chain extender, wherein each polycondensation reaction:
occurs from about 5 to about 5,000 times, and
involves a diisocyanate and a diol, diamine or dithiol chain extender that may be the same as or different than any other diisocyanate(s) and any other diol, diamine or dithiol chain extender(s) involved in any other polycondensation reaction(s).

7. The composition of claim 1, wherein the biodegradable copolymer further comprises a third segment A', and wherein the A' segment:
is made from at least one diisocyanate and at least one diol, diamine or dithiol chain extender;
has an $M_n$ from about 0.4 kDa to about 500 kDa;
may be attached to the B segment or the A segment; and
may be the same as or different than the A segment.

8. The composition of claim 7, wherein the A' segment is made from one to four different polycondensation reactions involving a diisocyanate and a diol, diamine or dithiol chain extender, wherein each polycondensation reaction:
occurs from about 5 to about 5,000 times, and
involves a diisocyanate and a diol, diamine or dithiol chain extender that may be the same as or different than any other diisocyanate(s) and any other diol, diamine or dithiol chain extender(s) involved in any other polycondensation reaction(s).

9. The composition of claim 7, wherein the A' segment is attached to the B segment.

10. The composition of claim 7, wherein the A' segment is attached to the A segment.

11. The composition of claim 7, wherein the A and A' segments are the same.

12. The composition of claim 7, wherein the A and A' segments are different.

13. The composition of claim 12, wherein the A' segment has a $T_g$ or $T_m$ in the range from about −70° C. to about 100° C.

14. The composition of claim 13, wherein the A' segment has a $T_g$ or $T_m$ in the range from about −20° C. to about 35° C.

15. The composition of claim 1, wherein the B segment is derived from a polyester containing at least one hydroxyl end group selected from the group consisting of polycaprolactone (PCL) diol, poly(β-hydroxy-alkanoate-diol), poly([R]-3-hydroxybutyrate-diol), poly(L-lactide) (PLLA) diol, poly(D,L-lactide) diol, polyglycolic acid, polyglycolide (PGA) diol, poly(trimethylene carbonate) (PTMC) diol, polydioxanone diol, polyvalerolactone diol, polypropiolactone diol, polyacetal, and hydroxyl-terminated random or block copolymers thereof.

16. The composition of claim 15, wherein the polyester containing at least one hydroxyl end group is selected from the group consisting of poly(trimethylene carbonate) (PTMC) diol, polydioxanone diol, polyvalerolactone diol, polypropiolactone diol, polyacetal, and hydroxyl-terminated random or block copolymers thereof.

17. The composition of claim 16, wherein the hydroxyl-terminated random or block copolymer is selected from the group consisting of poly(glycolide-co-trimethylene carbonate), poly(caprolactone-co-trimethylene carbonate), poly(glycolide-co-trimethylene carbonate-co-caprolactone), and any variations in the arrangement of the monomers thereof.

18. The composition of claim 1, wherein the B segment further comprises at least one non-fouling moiety.

19. The composition of claim 18, wherein the at least one non-fouling moiety is selected from the group consisting of polyethylene glycol (PEG), polypropylene glycol, poly(ethylene oxide-co-propylene oxide) surfactants, poly(2-hydroxyethyl methacrylate) (PHEMA), poly(vinyl alcohol) (PVA), polyalkene oxides, poly(n-propylmethacrylamide), poly(N-vinyl-2-pyrrolidone) (PVP), sulfonated polystyrene, dextran, sulfonated dextran, dextrin, hyaluronic acid, sodium hyaluronate, and derivatives thereof.

20. The composition of claim 1, wherein the A segment is made from at least one aliphatic diisocyanate.

21. The composition of claim 20, wherein the at least one aliphatic diisocyanate is selected from the group consisting of 1,2-diisocyanatoethane, 1,3-diisocyanatopropane, 1,4-diisocyanatobutane, 1,5-diisocyanatopentane, 1,6-diisocyanatohexane, 1,4-diisocyanatocubane, and lysine diisocyanate.

22. The composition of claim 1, wherein the A segment is made from at least one diol, diamine or dithiol chain extender selected from the group consisting of ethylene glycol, 1,3-propanediol, 1,2-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,2-cyclohexanedimethanol, 1,4-cyclohexanedimethanol, the corresponding diamine and dithiol analogs thereof, lysine ethyl ester, arginine ethyl ester, p-alanine-based diamine, and random or block copolymers made from at least one diisocyanate and at least one diol, diamine or dithiol chain extender.

23. The composition of claim 1, wherein the B segment is immiscible with the A segment.

24. The composition of claim 1, wherein the copolymer is thermoplastic.

25. The composition of claim 1, wherein the copolymer is thermoset.

26. The composition of claim 1, further comprising at least one additional biocompatible polymer.

27. The composition of claim 26, wherein the at least one biocompatible polymer is selected from the group consisting of poly(ethylene glycol) (PEG); polypropylene; poly(propylene glycol) (PPG); poly(N-vinyl pyrrolidone) (PVP); poly(N-vinyl pyrrolidone-co-vinyl acetate) (Copovidone); poly(ester amides) (PEA); acrylic acid (AA); polyacrylates; acrylamides; fluorinated polymers or copolymers; poly(hydroxyvalerate); poly(L-lactic acid)/polylactide (PLLA); poly(ε-caprolactone); poly(lactide-co-glycolide) (PLGA); poly(hydroxybutyrate); poly(hydroxyvalerate); poly(hydroxybutyrate-co-valerate); polydioxanone; polyorthoesters; polyanhydrides; poly(glycolic acid)/polyglycolide (PGA); poly(D,L-lactic acid) (PLA); poly(glycolic acid-co-trimethylene carbonate); polyphosphoesters; polyurethanes; polyureas; polyurethane(ureas); poly(amino acids); cyanoacrylates; poly(trimethylene carbonate); poly(iminocarbonates); co-poly(ether-esters); polyalkylene oxalates; polyphosphazenes; silicones; polyesters; polyolefins; polyisobutylene and ethylene-α-olefin copolymers; vinyl halide polymers and copolymers; polyvinyl ethers; polyvinylidene chloride; polyacrylonitrile; polyvinyl ketones; polyvinyl aromatics; polyvinyl esters; copolymers of vinyl monomers with each other; olefins; poly(vinyl alcohol) (PVA); acrylonitrile butadiene (ABS) resins; ethylene-vinyl acetate copolymers; polyamides; alkyl resins; polycarbonates; polyoxymethylenes; polyimides; polyethers; epoxy resins; rayon; rayon-triacetate; and combinations and co-polymers thereof.

28. The composition of claim 1, further comprising at least one biobeneficial material.

29. The composition of claim 28, wherein the at least one biobeneficial material is selected from the group consisting of fibrin; fibrinogen; cellulose and cellulose derivatives; starch; pectin; chitosan; elastin, gelatin; alginate and conjugates thereof; collagen and conjugates thereof; hyaluronan and derivatives thereof; hyaluronic acid; sodium hyaluronate; and self-assembled peptides (SAP).

30. The composition of claim 1, further comprising at least one biologically active agent selected from the group consisting of antiproliferative, antineoplastic, anti-inflammatory, antiplatelet, anticoagulant, antifibrin, antithrombin, antimitotic, antibiotic, antiallergic and antioxidant substances.

31. The composition of claim 30, wherein the at least one biologically active agent is selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, bioactive RGD, CD-34, antibody, abciximab (REOPRO), progenitor cell-capturing antibodies, prohealing drugs, prodrugs thereof, co-drugs thereof, and a combination thereof.

32. A coating comprising the composition of claim 1.

33. A coating comprising the composition of claim 30.

34. A coating comprising the composition of claim 31.

35. An implantable device formed of a material comprising the composition of claim 1.

36. The implantable device of claim 35, wherein the material is a coating disposed over the device.

37. The implantable device of claim 35, which is selected from the group consisting of stents, grafts, stent-grafts, catheters, leads and electrodes, clips, shunts, closure devices and valves.

38. An implantable device formed of a material comprising the composition of claim 30.

39. The implantable device of claim 38, wherein the material is a coating disposed over the device.

40. The implantable device of claim 38, which is selected from the group consisting of stents, grafts, stent-grafts, catheters, leads and electrodes, clips, shunts, closure devices and valves.

41. An implantable device formed of a material comprising the composition of claim 31.

42. A method of preparing the composition of claim 1, comprising:
performing polycondensation of a diisocyanate and a diol, diamine or dithiol chain extender with a B segment polymer containing at least one hydroxyl, amino or thiol end group, and
optionally performing additional polycondensation reaction(s) with additional diisocyanate(s) and additional diol, diamine or dithiol chain extender(s);
conjugating at least one dihydroxyaryl group to the polymer ends of the copolymer.

43. A method of fabricating an implantable device, comprising forming the device of material comprising the composition of claim 1.

44. A method of fabricating an implantable device, comprising forming the device of material comprising the composition of claim 30.

45. A method of treating or preventing a condition or disorder in a patient, comprising implanting in the patient an implantable device comprising a coating formed of a material comprising the composition of claim 1, wherein the condition or disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation for vein and artificial grafts, arteriovenous anastamoses, bile duct obstruction, ureter obstruction and tumor obstruction.

46. The method of claim 45, wherein the condition or disorder is selected from atherosclerosis, thrombosis, restenosis, and vulnerable plaque.

47. The method of claim 45, further comprising providing a thermal stimulus to the device if the $T_g$ or $T_m$ of the B segment is greater than body temperature.

48. The method of claim 45, wherein the composition further comprises at least one biologically active agent selected from the group consisting of antiproliferative, antineoplastic, anti-inflammatory, antiplatelet, anticoagulant, antifibrin, antithrombin, antimitotic, antibiotic, antiallergic and antioxidant substances.

49. The method of claim 48, wherein the at least one biologically active agent is selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, bioactive RGD, CD-34, antibody, abciximab (REOPRO), progenitor cell-capturing antibodies, prohealing drugs, prodrugs thereof, co-drugs thereof, and a combination thereof.

50. The method of claim 45, wherein the implantable device is selected from the group consisting of stents, grafts, stent-grafts, catheters, leads and electrodes, clips, shunts, closure devices and valves.

51. The composition of claim 1, wherein the dihydroxyaryl group contains a 3, 4-dihydroxyphenyl moiety or a 1, 2-dihydroxyphenyl moiety.

52. The composition of claim 51, wherein the 3, 4-dihydroxyphenyl moiety is formed from 3,4-dihydroxyhydrocinnamic acid or dopamine.

53. A method of preparing a composition of claim 12, wherein the A' segment is different than the A segment;
wherein when the A' segment is attached to the B segment to form A-B-A' trisegment copolymer, the method comprising the following steps:
performing polycondensation of a diisocyanate and a diol, diamine or dithiol chain extender with a B segment polymer containing a free hydroxyl, amino or thiol end group and a protected hydroxyl, amino or thiol end group;
optionally performing additional polycondensation reaction(s) with additional diisocyanate(s) and additional diol, diamine or dithiol chain extender(s);
protecting the functional group formed at the polymer end of the A segment;
deprotecting the protected hydroxyl, amino or thiol end group of the B segment;
performing polycondensation of a diisocyanate and a diol, diamine or dithiol chain extender with the deprotected hydroxyl, amino or thiol end group of the B segment;
optionally performing additional polycondensation reaction(s) with additional diisocyanate(s) and additional diol, diamine or dithiol chain extender(s); and
optionally deprotecting the protected functional group at the polymer end of the A segment;
or
wherein when the A' segment is attached to the A segment to form A'-A-B trisegment copolymer, the method comprising the following steps:
performing polycondensation of a diisocyanate and a diol, diamine or dithiol chain extender with a B segment polymer containing a free hydroxyl, amino or thiol end group and a protected hydroxyl, amino or thiol end group;
optionally performing additional polycondensation reaction(s) with additional diisocyanate(s) and additional diol, diamine or dithiol chain extender(s);
performing polycondensation of a diisocyanate and a diol, diamine or dithiol chain extender with the deprotected hydroxyl, amino or thiol end group of the A segment;
optionally performing additional polycondensation reaction(s) with additional diisocyanate(s) and additional diol, diamine or dithiol chain extender(s); and
optionally deprotecting the protected functional group at the polymer end of the B segment.

* * * * *